United States Patent [19]
Danishefsky et al.

[11] Patent Number: 5,386,019
[45] Date of Patent: Jan. 31, 1995

[54] SYNTHESIS OF INHIBITORS OF CALMODULIN-MEDIATED ENZYMES INCLUDING KS-501, KS-502 AND THEIR ENANTIOMERS

[75] Inventors: Samuel J. Danishefsky, New Haven, Conn.; Russell Dushin, Peekskill, N.Y.; William N. Hait, North Haven, Conn.

[73] Assignee: Yale University, New Haven, Conn.
[21] Appl. No.: 821,719
[22] Filed: Jan. 15, 1992
[51] Int. Cl.⁶ .................. C07H 1/00; C07H 13/02
[52] U.S. Cl. .................. 536/18.6; 536/4.1; 536/116; 536/118; 536/119; 536/120; 536/124; 536/125
[58] Field of Search .............. 536/18.6, 18.5, 124, 536/4.1, 115, 116, 120, 125; 556/436; 558/252; 560/67

[56] References Cited

U.S. PATENT DOCUMENTS

| | | | |
|---|---|---|---|
| 4,801,697 | 1/1989 | Yaginuma et al. | 536/4.1 |
| 4,868,159 | 9/1989 | Nakanishi et al. | 536/4.1 |
| 5,004,833 | 4/1991 | Yasuzawa et al. | 536/115 |

FOREIGN PATENT DOCUMENTS

| | | |
|---|---|---|
| 0282322 | 9/1988 | European Pat. Off. |
| 0360239 | 3/1990 | European Pat. Off. |
| 2579599 | 10/1986 | France |

OTHER PUBLICATIONS

Nakanishi et al., *J. Antibiotics* XLII (7), 1049–1055 (Jul. 1989).
Yasuzawa et al. *J. Antibiotics* XLIII, 336–343 (Apr. 1990).
Yaginuma et al., FR 2,579,599, 03 Oct. 1986 (abstract only).
Hait et al., *Molecular Pharmacology* 32, 404–409 (1987).
Hait et al., *Biochemical Pharmacology* 34(22), 3973–3978 (1985).
Hait et al., *J. Clin. Oncol.* 4(6), 994–1012 (Jun. 1986).
Dushin, R. J. and Danishefsky, S. J., "Total Syntheses of KS–501, KS–502 and Their Enantiomers" *J. of Am. Chem. Soc.*, 114(2): 655–659 (Feb. 1992).
Chemical Abstracts, vol. 108, No. 15, issued 11 Apr. 1988, Elix et al, "A Novel Synthesis of the Lichen Depsidones Divaronic Acid and Stenosporonic Acid, and the Biosynthetic Implications" see p. 714, col. 1, abstract No. 131402d, *Aust. J. Chem.* 1987, 40(8), 1451–64 (Eng).
Chemical Abstracts, vol. 110, No. 23, issued 05 Jun. 1989, Nakanishi et al, "Serotonin Inhibitors and their Manufacture with Sporothrix and Pharmaceutical Compositions Containing Them" see p. 592, col. 2, abstract No. 210960d, Eur. Pat. Appl. EP 286,330 (Cl. C12P1/06), 12, Oct. 1988.
Chemical Abstract, vol. 111, No. 3, issued 17 Jul. 1989, Yasuzawa et al, "Structure Determination of Calmoduline-Dependent Phosphodiesterase Inhibitors KS–501 and KS–502" see page 344, col. 1, abstract No. 205656, *Tennen Yuki Kagobutsu Toronkai Koen Yoshisha* 1988, 30, 65–72 (Japan).
Chemical Abstracts vol. 113, No. 5, issued 30 Jul. 1990, Nakanishi et al, "Serotonin Release-Inhibiting and Amnesia-Treating KS–502 and its Manufacture with Sporothrix" see p. 469, col. 2, abstract No. 38927X, Jpn. Kokai Tokkyo Koho JP 02 72,185 [90 72, 185] (Cl. C07H15/203), 12 Mar. 1990.
Chemical Abstracts, vol. 113, No. 17, issued 22 Oct. 1990, Yasuzawa et al, "Preparation of KS–501 Derivatives as Antithrombotic Agents" see page 832, column 1, abstract No. 152958h, Eur. Pat. Appl. EP 360,239 (Cl. C07H15/203) 28 Mar. 1990.
Chemical Abstracts, vol. 114, No. 20, issued 20 May 1991, Nakanishi et al "Pharmaceutical Composition Containing Benzoates as Cerebral Function Improvers" see p. 453, col. 1, abstract No. 192624y, Jpn. Kokai Tokkyo Koho JP 02,256,619 [90,256,619](Cl. A61K) 31/70), 17 Oct. 1990.

*Primary Examiner*—John W. Rollins
*Assistant Examiner*—Everett White
*Attorney, Agent, or Firm*—Hamilton, Brook, Smith & Reynolds

[57] ABSTRACT

The total synthesis of a group of compounds with inhibitory effects on calmodulin-mediated enzyme activities has been accomplished. Among these synthesized compounds are KS-501 and KS-502. Other compounds that have been synthesized by the described scheme are ent-KS-501 and ent-KS-502 which are enantiomers of KS-501 and KS-502 and which also have inhibitory effects on calmodulin-mediated enzyme activities.

43 Claims, 2 Drawing Sheets

SYNTHESIS OF INHIBITORS OF CALMODULIN-MEDIATED ENZYMES INCLUDING KS-501, KS-502 AND THEIR ENANTIOMERS

GOVERNMENT SUPPORT

This invention was made with U.S. Government support under PHS Grant HL25858 awarded by the NIH. The U.S. Government has certain rights in the invention.

BACKGROUND OF THE INVENTION

It is becoming increasingly apparent that many of the intracellular physiological activities in mammalian cells that involve $Ca^{2+}$ as a second messenger are mediated by calmodulin (CAM). This ubiquitous $Ca^{2+}$-binding protein has an ability to activate a variety of enzymes in a $Ca^{2+}$-dependent manner. Among these enzymes is $Ca^{2+}$ and calmodulin-dependent cyclic-nucleotide phosphodiesterase (CaM-PDE) and calmodulin-sensitive Kinase II (CaM-kinase II).

A variety of substances inhibit the activation properties of calmodulin on the calmodulin-dependent enzymes. It has been shown that drugs that inhibit calmodulin sensitive processes are also potent inhibitors of the growth and viability of tumor cells (Hait et al., . "Characterization of the Cytotoxic Effects of Calmodulin Inhibitors" *Biochem Pharmacol.* 34:3973-3978 (1985); Hait et al. "Calmodulin: A Potential Target for Cancer Chemotherapeutic Agents" *J. Clin. Oncol.* 4, 994-1012 (1986)). Thus, substances that inhibit calmodulin-mediated enzyme activites may affect cell viability, and possibly other cellular phenomena, through their interactions with calmodulin.

Recently, two new inhibitors of CaM-PDE were discovered (Nakanishi et al., "KS-501 and KS-502, New Inhibitors of $Ca^{2+}$ and Calmodulin-Dependent Cyclic-Nucleotide Phosphodiesterase from *Sporothrix* sp" *J. Antibiotics* 42:1049-1055 (1989)). These inhibitors of CaM-PDE are naturally occurring metabolites of the organism *Sporothrix* sp. KAC-1985 and have been designated KS-501 and KS-502 by their discoverers. The chemical structures of these inhibitory compounds are shown below:

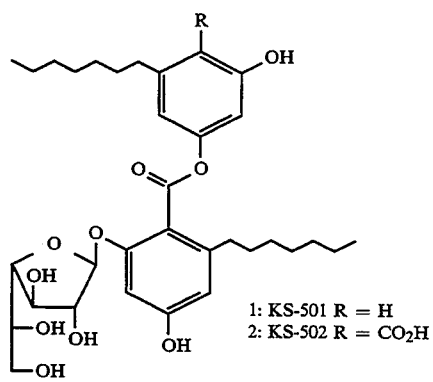

1: KS-501 R = H
2: KS-502 R = $CO_2H$

The KS-501 and KS-502 compounds inhibit CaM-dependent activities of CaM-PDE in the 1-5μM concentration range. Much higher concentrations of these compounds are required to inhibit CaM-independent activities of these enzymes. Furthermore, these compounds had no effect on protein kinase C which is another $Ca^{2+}$-dependent enzyme but which does not require calmodulin for its activity. Thus, the inhibitory properties of these compounds resides in their interactions with calmodulin.

These inhibitors of CaM-PDE, KS-501 and KS-502, are structurally similar to the naturally occurring compounds known as "TPI compounds" (Yaginuma et al., FR 2,579,599, 03 October 1986), differing only in the sugar content of the molecules. The "TPI compounds" are isolates of the organism Nodulisporium sp. M5220 which also display some inhibitory activity against phosphodiesterases. Currently, it is not known whether the "TPI compounds" inhibit the $Ca^{2+}$ and CaM-dependent enzymes.

To date, these inhibitory compounds, including KS-501 and KS-502, have been isolated as metabolic by-products of microorganisms. Since these microorganisms require facilities for their growth and maintenance, there is a need to produce these specific substances by organic synthetic routes in order to ensure an unlimited supply of these compounds. Even more importantly, such organic synthetic routes will enable the production of other compounds that possess the sought enzyme inhibitory activities, particularly the CaM-mediated enzyme inhibitory activities. These other compounds with CaM-mediated enzyme inhibitory activities will expand the available repertoire of such substances.

SUMMARY OF THE INVENTION

The present invention pertains to a method for producing the composition of the formula:

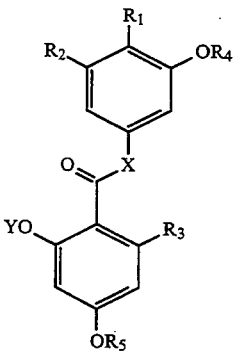

wherein the $R_1$ group can be either H, $CO_2H$, $CO_2$-lower alkyl or $CO_2$-benzyl; $R_2$ and $R_3$ can be either H or a $C_1$–$C_{20}$ saturated or unsaturated straight- or branched-chain alkyl group; $R_4$ and $R_5$ can be either H, Si-alkyl, Si-alkoxy, Si-aryl or benzyl; X can be either oxygen or sulfur and Y can be either a glycoside or H. In the latter instance of Y being H, an aglycone is formed. The selection of $R_3$ is independent of the selection of $R_2$; likewise, the selection of $R_5$ is independent of the selection of $R_4$.

In the present method of the invention, when Y is a glycoside, the method has two steps. In the initial step, a derivative of Y, which is a sugar glycal, is combined with a first 2,4-dihydroxybenzoic acid derivative, having the appropriate $R_3$ and $R_5$ substituents, under the appropriate chemical conditions so that covalent attachment of the sugar glycal to the first 2,4-dihydroxybenzoic acid derivative occurs through an oxygen atom at the 2 position of the first 2,4-dihydroxybenzoic acid derivative. This initial reaction produces an arylglycoside. In the second step, the just produced arylglycoside is combined with an aryl compound, having the appropriate $R_1$, $R_2$ and $R_4$ substituents, under the appropriate chemical conditions so that covalent attachment of the arylglycoside to the aryl compounds occurs through X. This second reaction produces the above-depicted composition where Y is a glycoside.

Alternatively, in the present method of the invention, when Y is H, the method has a single step. In this step, a 2,4-dihydroxybenzoic acid derivative, having the appropriate $R_3$ and $R_5$ substituents, is combined with an aryl compound, having the appropriate $R_1$, $R_2$ and $R_4$ substituents, under the appropriate chemical conditions so that covalent attachment of the 2,4-dihydroxybenzoic acid derivative to the aryl compound occurs through X. This produces the above-depicted aglycone.

The present invention also pertains to methods for producing KS-501, ent-KS-501, KS-502, and ent-KS-502. The ent-KS-501 and ent-KS-502 are the enantiomers or optical isomers of KS-501 and KS-502, respectively. In these methods, either 1,4-anhydro-3-0-benzyl-5,6-cyclopentylidene-2-deoxy-D-lyxo-hex-1-enofuranose or 1,4-anhydro-3-0-benzyl-5,6-cyclopentylidene-2-deoxy-L-lyxo-hex-1enofuranose is combined with $\beta$-trimethylsilylethyl 4-benzyloxy-6-(1-heptyn-1-yl)-2-hydroxy-benzoate to form [3'-benzyloxy-6'-carboxy-5'-(1-heptyn-l-yl)phenyl]-2,3-di-0-benzyl-5,6-cyclopentylidene-D-galactofuranoside or [3'-benzyloxy-6'-carboxy-5'-(1-heptyn-1-yl)phenyl]-2,3-di-0-benzyl-5,6-cyclopentylidene-L-galactofuranoside, respectively. Each of these latter compounds is combined with 5-heptyl-resorcinol under appropriate chemical conditions so that an esterification reaction occurs between a resorcinol hydroxyl and the carboxylate moiety of the respective galactofuranoside. The resulting compositions are, respectively, KS-501 and ent-KS-501. Alternatively, rather than combining each of the galactofuranosides with 5-heptyl-resorcinol, the respective galactofuranosides are each combined with benzyl 2,4-dihydroxy-6-(1-heptyl)-benzoate under appropriate chemical conditions so that an esterification reaction occurs between the 4-hydroxy moiety of the benzoate and the carboxylate moiety of the respective galactofuranoside. The resulting compositions of these latter esterification reactions are, respectively, KS-502 and ent-KS-502. The compounds ent-KS-501 and ent-KS-502 are produced as novel compositions by the methods of the present invention. Accordingly, these compositions, ent-KS-501 and ent-KS-502, also pertain to the present invention.

DETAILED DESCRIPTION OF THE INVENTION

Figure 1:
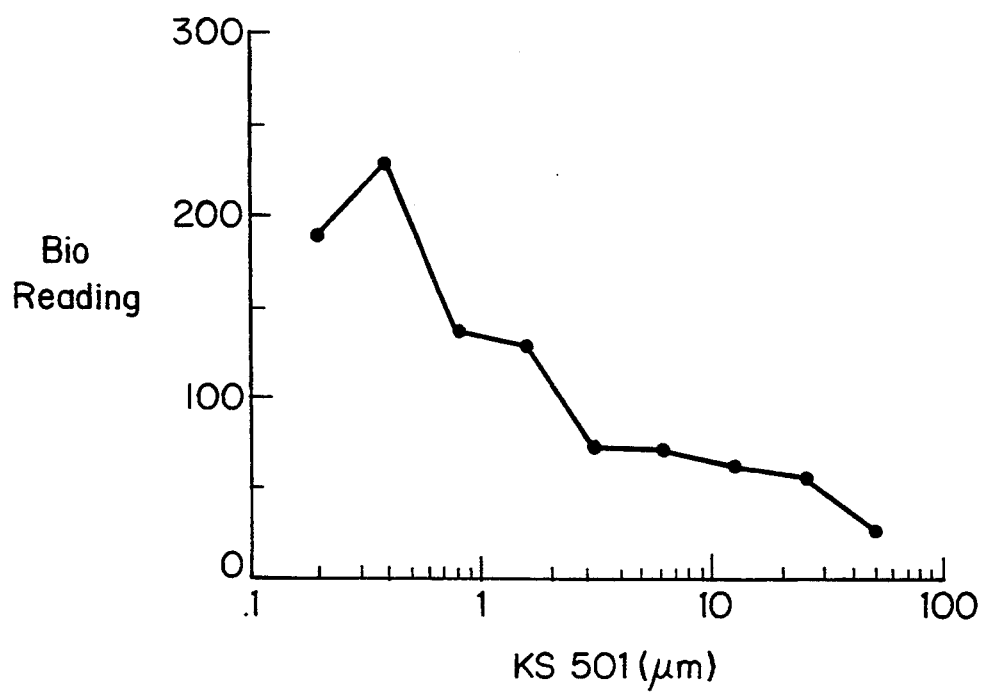
FIG. 1 is a graph showing the effect of various concentrations of KS-501 on the activity of $Ca^{2+}$/CaM-dependent phosphodiesterase.

This invention relates to compositions which have an inhibitory effect on calmodulin (CaM)-mediated enzyme activity. The basic structure of these compositions is depicted in the following structural formula:

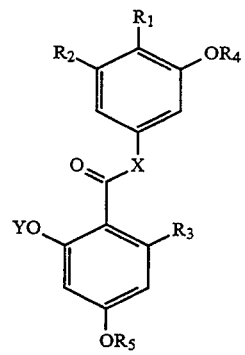

Two of the compositions produced by the methods of the present invention are KS-501 (1) and KS-502 (2). The chemical structures of these two compositions are embodied in the above structural formula. Other compositions are also produced by the methods of the present invention with chemical structures which are also embodied in the above structural formula. In particular, ent-KS-501 and ent-KS-502 are produced by the methods of the present invention. These latter compounds are novel compositions. They are the enantiomers of KS-501 and KS-502, respectively. These latter compounds have inhibitory effects on CaM-mediated enzyme activity which is similar to that of KS-501 and KS-502. That is, the enantiomers are not inactive isomers of KS-501 and KS-502 but, rather, possess inhibitory activity.

Other compositions can be produced in the present invention which also have inhibitory effects on phosphodiesterase activity and perhaps on CaM-mediated enzyme activity. These other compositions are the "TPI compounds". They have structural forms that are also embodied in the above structural formula. The "TPI compounds" differ from KS-501 and KS-502 only in the particular sugar or glycoside moiety (Y) that is present.

The above structural formula embodies a variety of specific compositions that possess demonstrable inhibitory effects on phosphodiesterase activity and particularly on CaM-mediated enzyme activities. Since these inhibitory effects are apparently not dependent on the glycoside moiety that is present, it is apparent that the inhibitory activity of this chemical family embodied by the above structural formula resides in the aglycone portion of this structural formula. That is, the inhibitory activity is apparently incorporated in the non-sugar portion of the above structural formula and is present when Y is hydrogen (H). The production of this aglycone is accomplished by methods of the present invention.

An embodiment of the present invention is the method for producing compositions having the above structural formula. In these compositions, $R_1$ is typically either H, $CO_2H$, $CO_2$-lower alkyl or $CO_2$-benzyl; $R_2$ and $R_3$ are typically and independently either H or a $C_1$–$C_{20}$ saturated or unsaturated straight- or branched-chain alkyl group; $R_4$ and $R_5$ are typically and independently either H, Si-alkyl, Si-alkoxy, Si-aryl or benzyl; X is interchangeablly either oxygen or sulfur; and Y is either a glycoside or H. The amount of saturation or branching of the alkyl groups of $R_2$ and $R_3$ is not critical. In particularly preferred embodiments of the invention, $R_2$ and $R_3$ are 1-heptyn-1-yl groups which subsequently become totally saturated. The use of oxygen or sulfur for X is also not critical. The chemical synthetic steps and chemical properties of the resulting compositions are similar when either oxygen or sulfur is at position X. In particularly preferred embodiments of the invention, X is oxygen.

In a preferred embodiment of the method of the present invention, Y is a glycoside. The method of this preferred embodiment has two steps. In the initial step, a derivative of the glycoside Y is combined with a 2,4-dihydroxybenzoic acid derivative, having appropriate $R_3$ and $R_5$ substituents, under conditions appropriate for covalent attachment or bonding to occur between the glycoside Y derivative and the 2,4-dihydroxybenzoic acid derivative. This covalent attachment occurs at the 2 position of the 2,4-dihydroxybenzoic acid derivative so that there is an oxygen atom bridge between the glycoside Y and the 2,4-dihydroxybenzoic acid derivative. In preferred embodiments of the method of the present invention, the derivative of the glycoside Y that combines with the 2,4-dihydroxybenzoic acid derivative is a sugar glycal. The conditions appropriate for the covalent attachment to occur between the sugar glycal and the 2,4-dihydroxybenzoic acid derivative are dependent on the reactants. In a preferred embodiment, an epoxidation of the sugar glycal is performed followed by reaction of the resulting epoxide with the 2,4-dihydroxybenzoic acid derivative. The resulting product of this initial step of combining the glycoside Y derivative with the 2,4-dihydroxybenzoic acid derivative is an arylglycoside.

In the second step of this preferred embodiment of the method of the present invention, the resulting arylglycoside is combined with an aryl compound, having appropriate $R_1$, $R_2$ and $R_4$ substituents, under conditions appropriate for covalent attachment or bonding to occur between the arylglycoside and the aryl compound. This covalent attachment occurs through X at the appropriate position of the aryl compound so that the composition having the above structural formula is formed. The conditions appropriate for the covalent attachment to occur between the arylglycoside and the aryl compound are dependent on the reactants. Often, a coupling reaction between these reactants is sufficient to produce products that can be easily converted into the final compositions with the above structural formula.

In preferred embodiments of the present invention, the glycoside is one of the following sugars: β-D-galactofuranoside, β-L-galactofuranoside, β-D-glucopyranoside, β-L-glucopyranoside, β-D-galactopyranoside or β-L-galactopyranoside. In particularly preferred embodiments of the present invention, the glycoside is either β-D-galactofuranoside or β-L-galactofuranoside. The β-D-galactofuranoside is the glycoside (Y) of KS-501 and KS-502 and the β-L-galactofuranoside is the glycoside (Y) of ent-KS-501 and ent-KS-502.

In further preferred embodiments of the method of the present invention, the aryl compound is either a resorcinol derivative or a second 2,4-dihydroxybenzoic acid derivative, in this instance having appropriate $R_2$ and $R_4$ substituents. When the aryl compound is a resorcinol derivative, $R_1$ can be a hydryl (H); by contrast, when the aryl compound is a second 2,4-dihydroxybenzoic acid derivative, $R_1$ can be either $CO_2H$, $CO_2$-lower alkyl or $CO_2$-benzyl. When either a resorcinol derivative or a second 2,4-dihydroxybenzoic acid derivative is the aryl compound, the covalent attachment to the arylglycoside occurs through an esterification reaction between the carboxylate group of the 2,4-dihydroxybenzoic acid derivative of the arylglycoside and either the 3-position hydroxyl of the resorcinol derivative or the 4-position oxygen of the second 2,4-dihydroxybenzoic acid derivative. The resulting ester linkage to the 3-position of the resorcinol derivative or the 4-position of the second 2,4-dihydroxybenzoic acid derivative yields compositions with the above structural formula. When a resorcinol derivative is used as the aryl compound, the resulting composition formed can be either KS-501 or ent-KS-501 depending on the glycoside (Y) incorporated into the structure. When a second 2,4-dihydroxybenzoic acid derivative is used as the aryl compound, the resulting composition formed can be either KS-502 or ent-Ks-502 again depending on the glycoside (Y) incorporated into the structure.

When a second 2,4-dihydroxybenzoic acid derivative is used as the aryl compound, the 4-position hydroxy is often protected prior to the covalent attachment or esterification reaction that occurs between this 2,4-dihydroxybenzoic acid derivative and the arylglycoside. Suitable protecting groups for this 4-position hydroxy include H, Si-alkyl, Si-alkoxy, Si-aryl, and benzyl moieties.

In preferred embodiments of the method of the present invention, the hydroxy positions of the glycoside (Y) derivative, particularly the sugar glycal, can have attached protective groups. These protective groups include, for example, H, alkyl, cycloalkyl, Si-alkyl, Si-alkoxy, Si-aryl or benzyl groups. These protective groups can be attached or removed at any time during the chemical procedures that eventually result in the compositions of the above structural formula. Usually, the final compositions have all protective groups removed with the exception of H so that hydroxyl groups remain at the hydroxy positions of the glycoside (Y).

In particularly preferred embodiments of the method of the present invention, when the glycoside (Y) is a galactofuranoside and the glycoside (Y) derivative is a furanose sugar glycal, a monosubstituted or disubstituted dioxolane can be formed which acts as a protective group for hydroxy positions of the furanose glycal. The substituents for the substituted dioxolane can be, for example, H, alkyl or cycloalkyl Again, this protective group can be chemically deprotected, e.g. by hydrolysis, to yield hydroxyl groups at the appropriate hydroxy positions of the glycoside.

The sugar glycal in particularly preferred embodiments of the method of the present invention is either 1,4-anhydro-3-0-benzyl-5,6-cyclopentylidene-2-deoxy-D-lyxo-hex-1-enofuranose or 1,4-anhydro-3-0-benzyl-5,6-cyclopentylidene-2-deoxy-L-lyxo-hex-1-enofuranose. That is, either the D form or the L form of the enofuranose is formed and used in these preferred embodiments. In further preferred embodiments, the D form of the enofuranose is formed from D-talose as a starting material and KS-501 or KS-502 can be produced; in contrast, the L form of the enofuranose is formed from L-talonic acid-g-lactone as a starting material and ent-KS-501 or ent-KS-502 can be produced.

The 2,4-dihydroxybenzoic acid derivative that becomes covalently attached to the glycoside (Y) derivative is β-trimethylsilylethyl 4-benzyloxy-6-(1-heptyn-1-yl)-2-hydroxy-benzoate in particularly preferred embodiments of the method of the present invention. The resorcinol derivative that can form the aryl compound is 5-heptyl-resorcinol in other particularly preferred embodiments of the method of the present invention. The second 2,4-dihydroxybenzoic acid derivative that can form the aryl compound is benzyl 2,4-dihydroxy-6-(1-heptyl)-benzoate in still other particularly preferred embodiments of the method of the present invention. Each of these three intermediates in the particularly preferred embodiments can be synthesized from 2,4,6-trihydroxybenzoic acid.

In preferred embodiments of the method of the present invention when X is sulfur, the glycoside (Y) can be one of the six sugars enumerated above which also can be formed from sugar glycals. The hydroxy positions of the glycoside (Y) derivative, i.e. the sugar glycal, can have attached protective groups as previously described. The $R_1$, $R_2$, $R_3$, $R_4$ and $R_5$ groups can be the same as those in the analogous positions of KS-501 or KS-502. The sugar glycals can be the same as those described above in the particularly preferred embodiments of these glycals and they also can be formed from the starting materials as described above.

In preferred embodiments of the method of the present invention when Y is H, the method has just one step. In this step, a 2,4-dihydroxybenzoic acid derivative, having appropriate $R_3$ and $R_5$ substituents, is combined with an aryl compound, having appropriate $R_1$, $R_2$ and $R_4$ substituents, under conditions appropriate for covalent attachment or bonding to occur between the 2,4-dihydroxybenzoic acid derivative and the aryl compound. This covalent attachment occurs through X at the appropriate position of the aryl compound so that the composition having the above structural formula is formed. The conditions appropriate for the covalent attachment to occur between the 2,4-dihydroxybenzoic acid derivative and the aryl compound are dependent on the reactants. Often, a coupling reaction is sufficient to produce products that can be easily converted into the final compositions. For example, after the covalent attachment reaction, the $R_2$ and $R_3$ groups can be easily converted to saturated $C_7$ straight chain alkyl groups. In particularly preferred embodiments of the method, the $R_1$, $R_2$, $R_3$, $R_4$ and $R_5$ groups can be the same as those in the analogous positions of KS-501 or KS-502. In further preferred embodiments of the method, X is oxygen and the 2,4-dihydroxybenzoic acid derivative and aryl compound can be the intermediates described above when Y was a glycoside (i.e. β-trimethylsilylethyl 4-benzyloxy-6-(1-heptyn-1-yl)-2-hydroxy-benzoate and 5-heptyl-resorcinol or benzyl 2,4-dihydroxy-6-(1-heptyl)-benzoate, respectively).

In other preferred embodiments of the present invention, the compositions KS-501, ent-KS-501, KS-502 and ent-KS-502 are each produced from specific materials previously described. For example, KS-501 is produced by first combining 1,4-anhydro-3-0-benzyl-5,6-cyclopentylidene-2-deoxy-D-lyxo-hex-1-enofuranose with β-trimethylsilylethyl 4-benzyloxy-6-(1-heptyn-1-yl)- 2-hydroxy-benzoate, each having been previously provided, under appropriate conditions to form [3'-benzyloxy-6'-carboxy-5'-(1-heptyn-1-yl)phenyl]-2,3-di-0-benzyl-5,6-cyclopentylidene-D-galactofuranoside. This compound is then combined with 5-heptyl-resorcinol under conditions appropriate for esterification to occur between a resorcinol hydroxyl and the carboxylate moiety of the product of the first reaction. KS-501 is thereby formed.

Similarly, ent-KS-501 is formed from 1,4-anhydro-3-O-benzyl-5,6-cyclopentylidene-2-deoxy-L-lyxo-hex-1-enofuranose, β-trimethylsilylethyl 4-benzyloxy-6-(1-heptyn-1-yl)-2-hydroxy-benzoate and 5-heptyl-resorcinol. In a similar manner, KS-502 is formed from 1,4-anhydro-3-0-benzyl-5,6-cyclopentylidene-2-deoxy-D-! yxo-hex-1-enofuranose, β-trimethylsilylethyl 4-benzyloxy-6-(1-heptyn-1-yl)-2-hydroxy-benzoate and benzyl 2,4-dihydroxy-6-(1-heptyl)-benzoate. The second reaction occurs at the 4-hydroxy position of the latter benzoate. In a similar manner, ent-KS-502 is formed from 1,4-anhydro-3-0-benzyl-5,6-cyclopentylidene-2-deoxy-L-lyxo-hex-1-enofuranose, β-trimethylsilylethyl 4-benzyloxy-6-(1-heptyn-1-yl)-2-hydroxy-benzoate and benzyl 2,4-dihydroxy-6-(1-heptyl)-benzoate.

In these latter preferred embodiments of the present invention, the D-enofuranoses can be synthesized from D-talose, the L-enofuranoses can be synthesized from L-talonic acid-g-lactone and the aryl compounds can be synthesized from 2,4,6-trihydroxybenzoic acid as previously described.

The compositions designated ent-KS-501 and ent-KS-502 are also embodiments of the present invention. These compositions can be produced by the previously described methods of the present invention.

Figure 2:
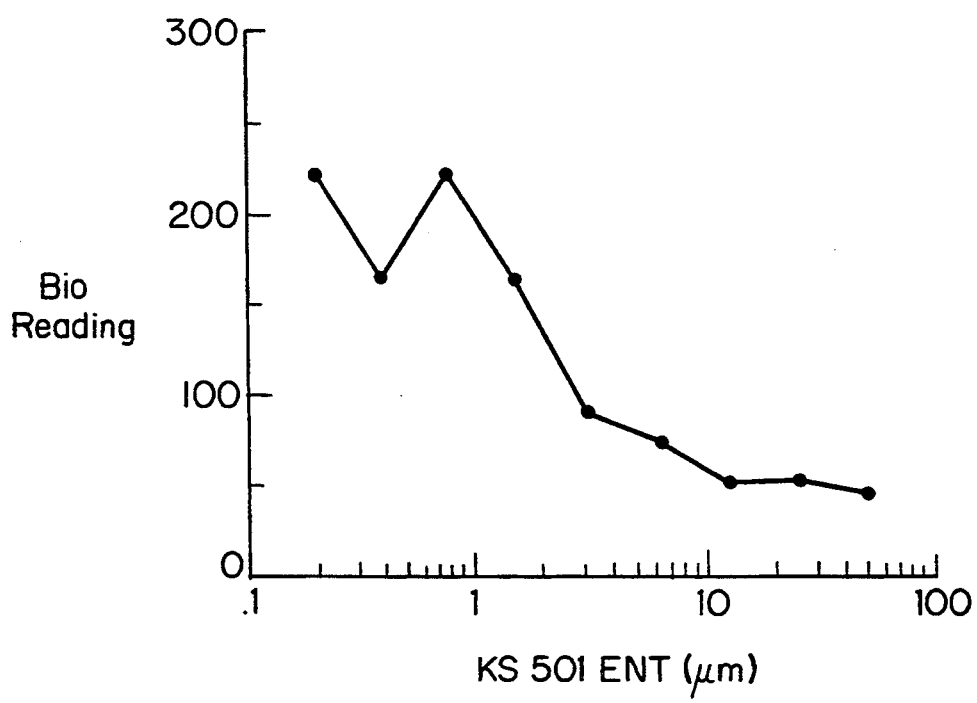
FIG. 2 is a graph showing the effect of various concentrations of ent-KS-501 on the activity of $Ca^{2+}$/CaM-dependent phosphodiesterase.
Figure 3:
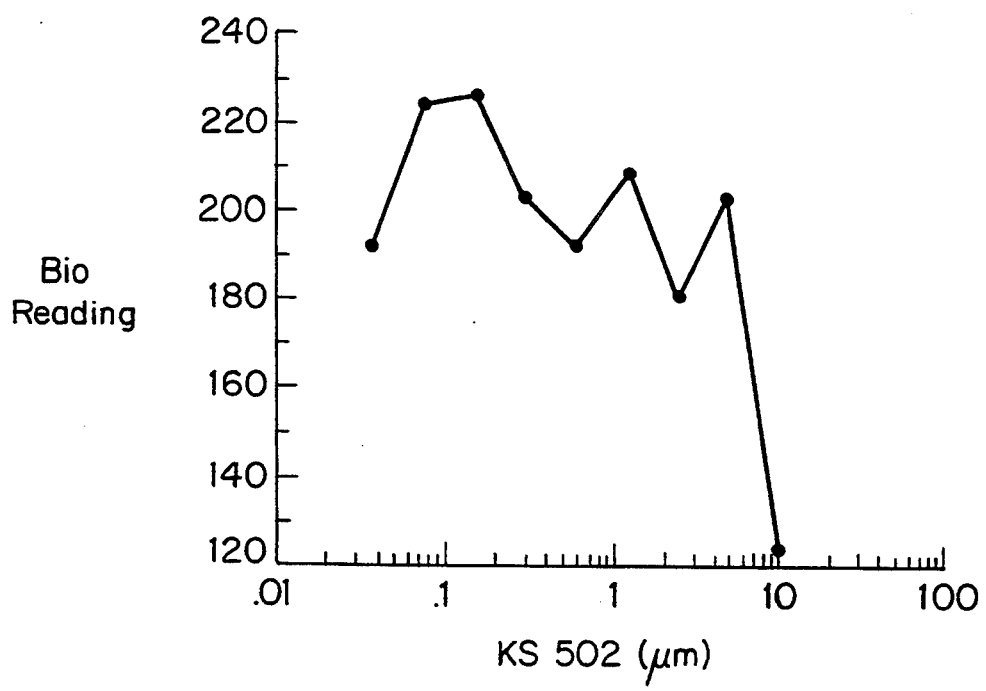
FIG. 3 is a graph showing the effect of various concentrations of KS-502 on the activity of $Ca^{2+}$/CaM-dependent phosphodiesterase.
Figure 4:
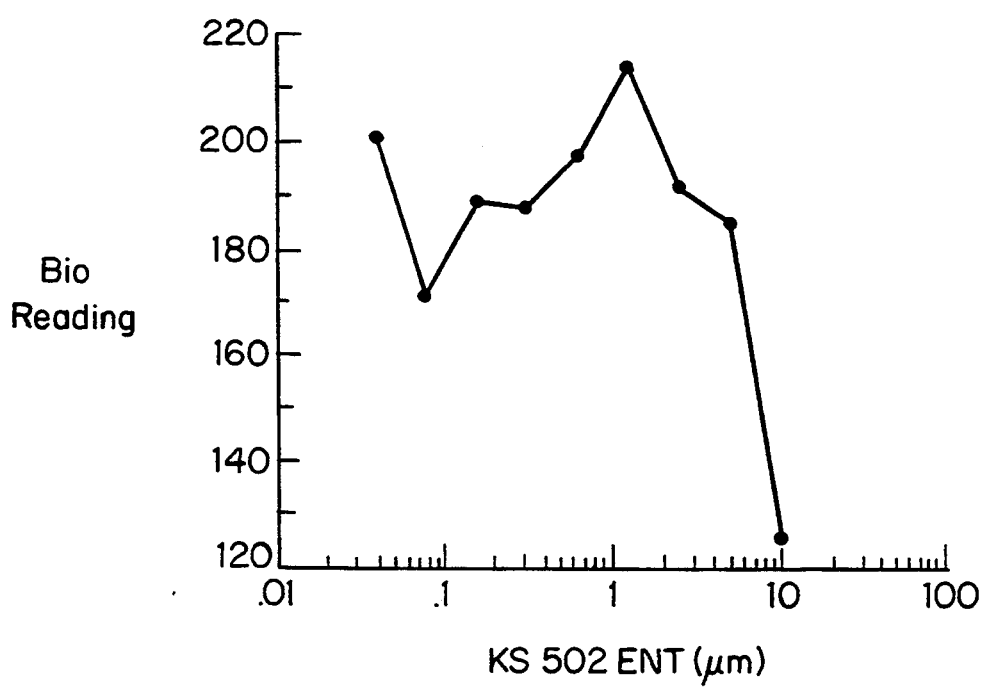
FIG. 4 is a graph showing the effect of various concentrations of ent-KS-502 on the activity of $Ca^{2+}$/CaM-dependent phosphodiesterase.

The inhibitory effects of the compositions KS-501, ent-KS-501, KS-502 and ent-KS-502 are shown in Table 1 and in FIGS. 1–4.

TABLE I

KS-501 & ent-KS-501 as Inhibitors of Ca++/Calmodulin PKC PKA Kinases

A)

(pmole/mg protein/min)

| | Basal | | | | | | Ca++/CaM | | | | |
|---|---|---|---|---|---|---|---|---|---|---|---|
| Site of Phos. in Synapsin I | Basal | KS-501 10 μM | KS-501 40 μM | ent-KS-501 10 μM | ent-KS-501 40 μM | Ca++ 1.5 mM | Ca++ CaM 3 μg | TFP 40 μM | KS-501 10 μM | KS-501 40 μM | ent-KS-501 10 μM | ent-KS-501 40 μM |
| 2,3 | 0.016 | 0.017 | 0.015 | 0.018 | 0.018 | 0.091 | 0.125 | 0.010 | 0.087 | 0.012 | 0.076 | 0.021 |
| 1 | 0.022 | 0.025 | 0.017 | 0.023 | 0.019 | 0.056 | 0.049 | 0.018 | 0.054 | 0.011 | 0.043 | 0.012 |

B)

(pmole/mg protein/min)

| | Basal | | | | | | Ca++/PSD | | | | |
|---|---|---|---|---|---|---|---|---|---|---|---|
| Site of Phos. in Synapsin I | Basal | KS-501 10 μM | KS-501 40 μM | ent-KS-501 10 μM | ent-KS-501 40 μM | Ca++ 1.5 mM | Ca++ PSD | PKC inh peptide 2 μM | KS-501 10 μM | KS-501 40 μM | ent-KS-501 10 μM | ent-KS-501 40 μM |
| 2,3 | 0.016 | 0.015 | 0.015 | 0.015 | 0.014 | 0.068 | 0.079 | 0.074 | 0.061 | 0.030 | 0.067 | 0.02 |
| 1 | 0.018 | 0.020 | 0.016 | 0.018 | 0.013 | 0.041 | 0.045 | 0.046 | 0.041 | 0.017 | 0.047 | 0.01 |

C)

TABLE I-continued

KS-501 & ent-KS-501 as Inhibitors of Ca++/Calmodulin PKC PKA Kinases

| | | Basal (pmole/mg protein/min) | | | | | | cAMP | | | |
|---|---|---|---|---|---|---|---|---|---|---|---|
| Site of Phos. in Synapsin I | Basal | KS-501 10 µM | KS-501 40 µM | ent-KS-501 10 µM | ent-KS-501 40 µM | cAMP 1 µM | cAMP + PKItide 1 µM | KS-501 10 µM | KS-501 40 µM | ent-KS-501 10 µM | ent-KS-501 40 µM |
| 2,3 | 0.007 | 0.008 | 0.007 | 0.006 | 0.010 | 0.008 | 0.014 | 0.008 | 0.009 | 0.009 | 0.008 |
| 1 | 0.028 | 0.033 | 0.015 | 0.025 | 0.017 | 0.041 | 0.019 | 0.049 | 0.025 | 0.049 | 0.03 |

The results represent the mean of 3 experiments
Site 2, 3 are known to be phosphorylated by Ca++/CaM dependent Kinase II
Site 1 is phosphorylated by both CaM KI and cAMP dependent kinase.
Therefore in the reaction of CaMK or PKC, PKA inhibitor is included in the reaction mix. And in the reaction of PKA, EGTA is included.
In vitro PKC is able to phosphorylate Synapsin I at all 3 serine sites.

The compositions KS-501 and ent-KS-501 are each inhibitory of $Ca^{2+}$/CaM-sensitive phosphodiesterase in the concentration range of 1–2µM. The compositions KS-502 and ent-KS-502 are each inhibitory of $Ca^{2+}$/CaM-sensitive phosphodiesterase in the concentration range of approximately 10µM. In addition, the compositions KS-501 and ent-KS-501 are each inhibitory of CaM-sensitive Kinase II in the concentration range of 10–40µM. It is readily apparent that these four (4) compositions have inhibitory effects on CaM-mediated enzyme activities. It is also readily apparent that the inhibitory effects of the enantiomeric compounds mimic the inhibitory effects of the originally isolated compounds both in terms of the targets of their inhibitory effects and in the sense of the quantities that have inhibitory activity.

The data in Table I also indicate that the compositions KS-501 and ent-KS-501 have more inhibitory activity against CaM-dependent kinases than against cAMP-dependent kinase or protein kinase C. Thus, it appears that the compositions of the present invention may possess more inhibitory effects against CaM-mediated enzyme activity than against CaM-independent enzyme activity To be effective as drugs in humans or other animals, the compositions of the present invention must be administered in an appropriate form to the individual. The compositions of the present invention can be administered by any route that allows a sufficient quantity of the drug to be introduced into the body. That is, they can be administered orally, rectally, topically, or by injection. The delivered form of the compositions of the present invention is determined by the route by which they are given. That is, they can be in the form of a capsule, tablet or oral liquid suspension, suppository, cream or ointment, or injectable liquid suspension.

The most common form of these compositions as drugs is as a capsule or tablet. In this form, administration is achieved by swallowing one or more capsules or tablets. This can be followed by further administration at designated time intervals, e.g. every 4 hours as the need for such a drug's effect is desired.

A preferred embodiment of the present method of synthesis of KS-501, KS-502 and related compounds is described in the immediately following paragraphs.

A schematic route for this embodiment accompanies this description. The numbers in parentheses in this description correspond to the numbers that designate the compounds in the schematic representation.

In this preferred embodiment of the present method of synthesis of KS-501, KS-502 and related compounds of this invention, a protected sugar (e.g., furanose glycal) is a useful intermediate. Such an intermediate can be readily prepared using known methods (see e.g., Ireland et al., J. Org. Chem. 43, 786 (1978) or Ireland et al., J. Org. Chem. 45, 48 (1980)).

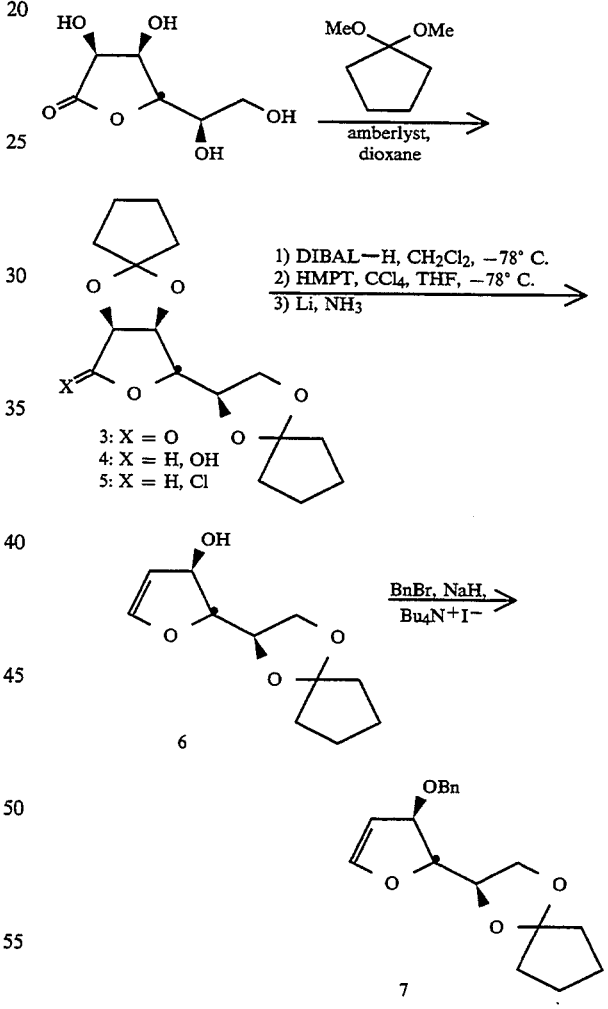

For example, D-talonic acid lactone can be protected as its bis (cyclopentylidene) acetal (3) and then reduced with DIBAH in methylene chloride to give hemiacetal (4). Treatment of hemiacetal (4) with hexamethylphosphoroustriamide-carbon tetrachloride gives the anomeric chloride (5). Reduction of the anomeric chloride (5) with lithium in ammonia, followed by benzylation (or addition of another protective group) of the resultant enofuranose (6) (NaH, BnBr, THF) results in the production of the protected sugar (furanose glycal) (7).

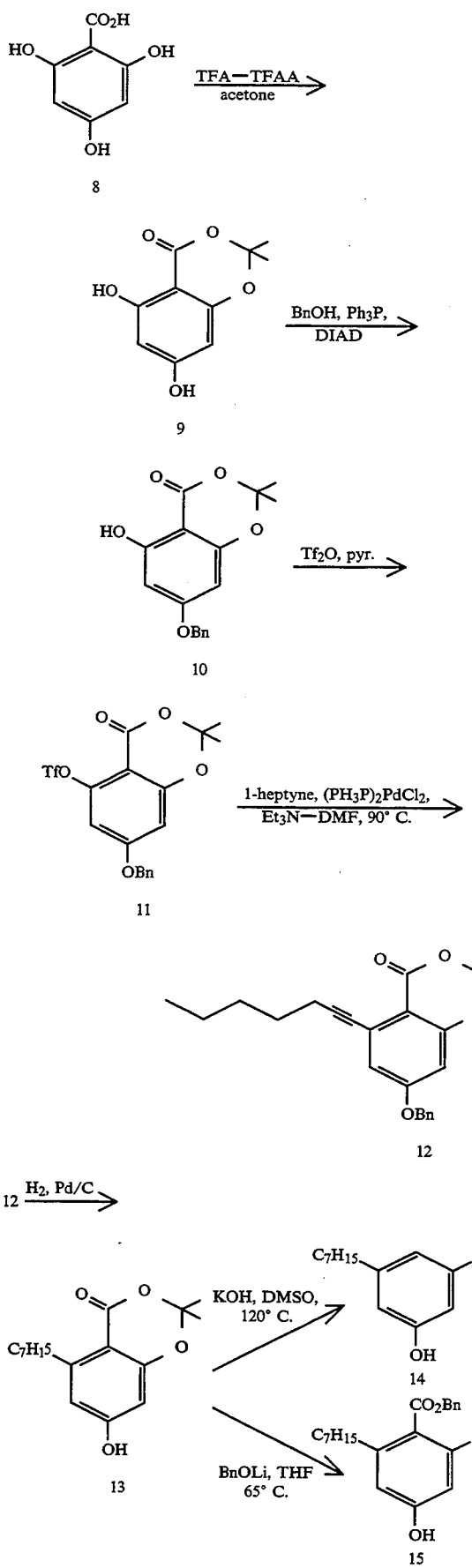

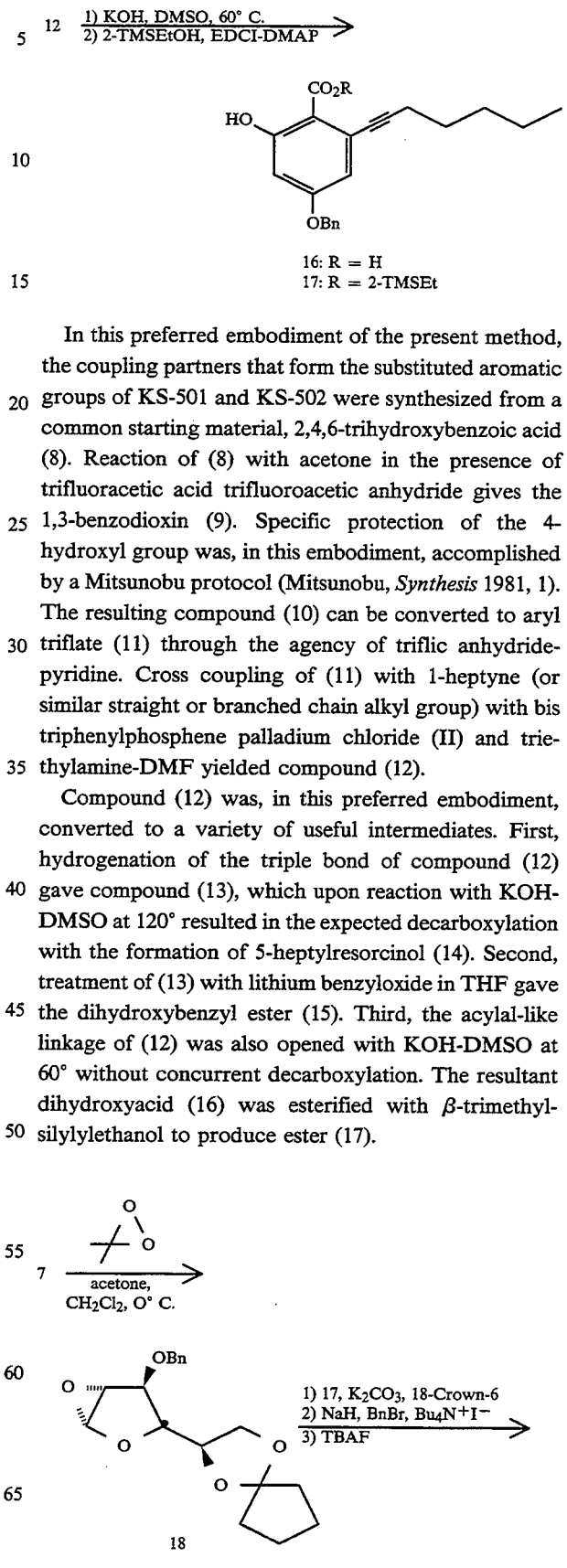

16: R = H
17: R = 2-TMSEt

In this preferred embodiment of the present method, the coupling partners that form the substituted aromatic groups of KS-501 and KS-502 were synthesized from a common starting material, 2,4,6-trihydroxybenzoic acid (8). Reaction of (8) with acetone in the presence of trifluoroacetic acid trifluoroacetic anhydride gives the 1,3-benzodioxin (9). Specific protection of the 4-hydroxyl group was, in this embodiment, accomplished by a Mitsunobu protocol (Mitsunobu, *Synthesis* 1981, 1). The resulting compound (10) can be converted to aryl triflate (11) through the agency of triflic anhydride-pyridine. Cross coupling of (11) with 1-heptyne (or similar straight or branched chain alkyl group) with bis triphenylphosphene palladium chloride (II) and triethylamine-DMF yielded compound (12).

Compound (12) was, in this preferred embodiment, converted to a variety of useful intermediates. First, hydrogenation of the triple bond of compound (12) gave compound (13), which upon reaction with KOH-DMSO at 120° resulted in the expected decarboxylation with the formation of 5-heptylresorcinol (14). Second, treatment of (13) with lithium benzyloxide in THF gave the dihydroxybenzyl ester (15). Third, the acylal-like linkage of (12) was also opened with KOH-DMSO at 60° without concurrent decarboxylation. The resultant dihydroxyacid (16) was esterified with β-trimethylsilylylethanol to produce ester (17).

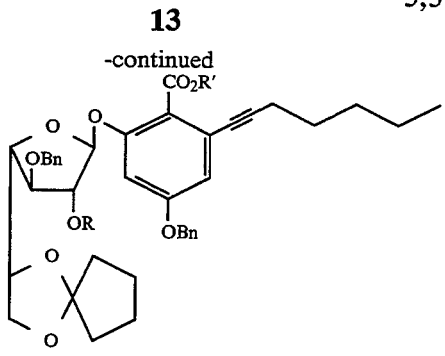

19: R = H, R' = 2-TMSEt
20: R = Bn, R' = 2-TMSEt
21: R = Bn, R' = H

21 $\xrightarrow{\text{1) 14, EDCI—DMAP}}_{\text{2) TsOH, MeOH}}$

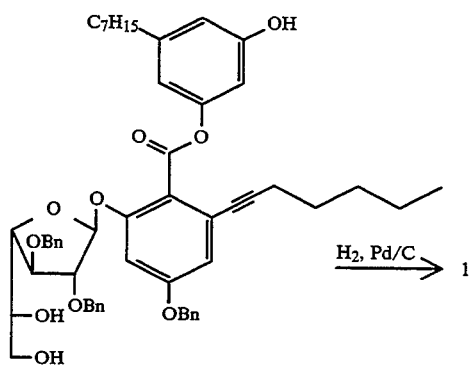

22

21 $\xrightarrow{\text{1) 15, EDCI—DMAP}}_{\text{2) TsOH, MeOH}}$

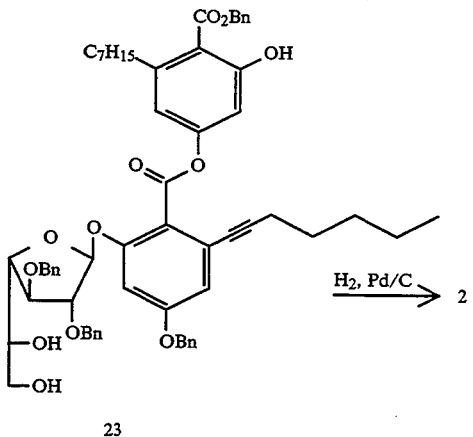

23

With the formation of compounds (7), (14), (15) and (17), the final synthesis of KS-501, KS-502 and their enantiomers can proceed. The program for combining these building blocks commences with epoxidation of sugar glycal (7) (1 eq of 2,2-dimethyldioxirane in methylene chloride- acetone). Reaction of (17) with the epoxide (18) (K$_2$CO$_3$, 18-Crown-6, acetone) resulted in the production of arylglycoside (19). The secondary alcohol function of (19) was benzylated to provide compound (20). Unveiling of the carboxylic acid (TBAF; THF) leads to compound (21). Coupling of (21) with (14) (EDCI-DMAP) followed by hydrolysis of the 5,6-cyclopentylideneacetal (TsOH-MeOH) gave compound (22). Exposure of this compound to the action of hydrogen (Pd/C) in ethanol resulted in hydrogenation of the triple bond and concurrent hydrogenolytic cleavage of all three benzyl protecting groups with the formation of KS-501. Alternatively, acylation of (15) with (21) (EDCI; DMAP) has been found in the present method to occur specifically at the p-hydroxyl group. Cleavage of the cyclopentylidene group can again be accomplished through the action of TsOH in methanol. Finally, hydrogenation of (23) over Pd/C resulted in reduction of the triple bond and cleavage of the four benzyl protecting groups with the resulting formation of KS-502. The fully synthetic products, KS-501 and KS-502, are identical with those produced by natural materials as shown by $^1$H NMR, UV, optical rotation and tlc mobilities in a variety of solvents.

The enantiomers of KS-501 and KS-502, namely ent-KS-501 and ent-KS-502, were produced by the foregoing synthetic procedure by substituting L-talonic acid lactone for D-talose as a starting material. The L-talonic acid lactone can be easily formed from L-ascorbic acid (Posset al, Tetrahedron Lett. 30, 5201 (1989)).

The invention is illustrated by the following Exemplification. This Exemplification is not to be viewed as being limiting of the invention.

EXEMPLIFICATION

Preparation of KS-501, KS-502, ent-KS-501 and ent-KS-502 a. Formation of Protected Furanose.

2,3,5,6,-Dicyclopentylidene-D-talonic acid-g-lactone (3).

A solution of D-talose (500 mg, 2.78 mmol) in water (3.3 mL) was treated with CaCO$_3$ (380 mg, 3.8 mmol) and Br$_2$ (165 μL, 510 mg, 3.2 mmol, 1.15 eq) and the mixture was stirred for 24 hrs. at room temperature. The solution was then filtered, passed through a 0.5×0.5 in. column of Amberlite IR-120 ™ with methanol, and concentrated to give 590 mg of crude talonic acid-γ-lactone as a brown gum. A solution of this crude material (2.78 mmol) in dioxane (7 mL) was treated with 1,1-dimethoxycyclopentane (4.5 mL) and amberlyst-15 ™ (30 mg). After stirring overnight the solution was filtered, diluted with EtOAc, washed with water, saturated aqueous NaHCO$_3$, water, brine, and dried over MgSO$_4$. Concentration, chromatography over silica gel (eluted with 18% EtOAc-hexanes), and crystallization gave 494 mg (57%) of (3) as white needles. m.p. 129°–130° C. [α]$^{22}$$_D$=+33.0° (c. 1.09, CHCl$_3$); IR (CHCl$_3$) 3020, 2960, 1790, 1340, 1185, 1120, 97 cm$^{-1}$; $^1$H NMR (CDCl$_3$, 250 MHz) δ4.77 (d, 1H, J=5.7 Hz, H-2), 4.70 (d, 1H, J=5.7 Hz, H-3), 4.57 (d, 1H, J=1Hz, H-4), 4.22 (ddd, 1H, J=6.9, 6.8, 1Hz, H-5), 4.07 (dd, 1H, J=8.3, 6.8 Hz, H-6), 3.95 (dd, 1H, J=8.3, 6.8 Hz, H-6 ') , 1.58–1.98 (m, 16H) .

2,3,5,6,-Dicyclopentylidene-L-talonic acid-g-lactone (ent-3).

A solution of L-talonic acid-g-lactone (356 mg, 2 mmol) in dioxane (5 mL) was treated with 1,1-dimethoxycyclopentane (5 mL) and Amberlyst-15 ™ (30 mg) and the solution was stirred at room temperature for 12 hrs. The mixture was then filtered, diluted with EtOAc, washed with water, saturated aqueous NaHCO$_3$, water, brine, and dried over MgSO$_4$. Concentration and crystallization from a minimal amount of EtOAc in hexanes gave 355 mg of fine needles. Chromatography of the mother liquor over silica gel (eluted with 18% EtOAc-hexanes) yielded an additional 255 mg (610 mg total, 98%) of product as white solids. m.p. 129°1∝130° C. $[\alpha^{22}{}_D = -28.4°$ (c. 1.08, CHCl$_3$). MS M/e (relative intensity) 310 (22.2), 281 (100), 253 (8.1), 153 (17.6), 139 (9.3), 97 (10.6), 69 (19.3), 55 (35.5). Anal. Calcd for $C_{16}H_{22}O_6$: C, 61.92; H, 7.15. Found: C, 61.63; H, 7.03.

1,4-Anhydro-5,6-cyclopentylidene-2-deoxy-D-lyxo-hex-1-enofuranose (6).

A solution of lactone (3) (250 mg, 0.80 mmol) in CH$_2$Cl$_2$ (8 mL) at −78° C. was treated with DIBAL-H (1 M in CH$_2$Cl$_2$, 1.05 mL, 1.05 mmol, 1.3 eq). After stirring 1 hr the reaction was quenched with MeOH (0.5 mL), saturated aqueous Na/K tartarate (5 mL) was added, and the solution was allowed to stir at 0° C. for 1 hr. The mixture was filtered through Celite™, and the filtrate was washed twice with water, with brine, and dried over MgSO$_4$. Concentration left 250 mg (100%) of nearly pure hemiacetal (4) as a colorless oil. IR (CHCl$_3$) 3200-3600, 2970, 2880, 1440, 1345, 1115, 1055, 990 cm$^{-1}$; $^1$H NMR (250 MHz, CDCl$_3$) δ5.45 (dd, 1H, J=4.1, 11.1 Hz, H1, α-anomer), 5.37 (d, 1H, J=10.1 Hz, H1, β-anomer), 4.73 (m, 1H, H2, α- and β-anomers), 4.57 (dd, 1H, J=4.1, 6.3 Hz, H3, -anomer), 4.49 (d, 1H, J=6.0 Hz, H3, β-anomer), 4.31 (dd, 1H, J-1.3, 3.0 Hz, H4, β-anomer), 4.18 (dd, 1H, J=1.2, 3.0 Hz, H4, α-anomer), 4.10-4.16 (m, 1H, H5, α- and β-anomers), 3.83-4.07 (m, 2H, H6, α- and β-anomers), 1.67-2.04 (m, 16H).

The aforementioned hemiacetal (0.80 mmol) in THF (8 mL) at −78° C. was treated with CCl$_4$ (150 µL) and HMPT (85%, 180 µL, 137 mg, 0.83 mmol, 1.04 eq). After 10 mins. the resulting crude anomeric chloride (5) was cannulated into a cooled (−78° C.) solution of Li metal (370 mg, 52.9 mmol, 66 eq) in ammonia (30 mL). The mixture was refluxed for 2.5 hrs. and then the reaction was quenched with the careful addition of solid NH$_4$Cl (2.7 g) and 2-PrOH (5 mL). The resulting slurry was partitioned between Et$_2$O and water and the aqueous layer was extracted three times with Et$_2$O. Pooled organics were washed with brine, dried (MgSO$_4$), evaporated to dryness, and rapidly chromatographed over silica gel (eluted with 30% EtOAc in hexanes) to give 116 mg (68%) of (6) as a clear colorless oil $[\alpha]^{23}{}_D = =232.5°$ (c. 1.14, CHCl$_3$); IR (CHCl$_3$) 3300-3600, 3010, 2985, 1615, 1340, 1150, 1110, 1080 cm$^{-1bl}$; $^1$H NMR (CDCl$_3$, 250 MHz) δ6.58 (dd, 1H J=0.8 Hz, 2.6 Hz, Hi), 5.20 (t, 1H, J=2.6 Hz, H2), 4.73 (br m, 1H, H3), 4.30 (dd, 1H, J=3.2, 6.4 Hz, H4), 4.13 (ddd, 1H, J=6.0, 6.4, 6.7 Hz, H5), 4.00 (dd 1H, J=6.7, 8.4 Hz, H6), 3.87 (dd, 1H, J=6.0, 8.4 Hz, H6').

1,4-Anhydro-5,6-cyclopentylidene-2-deoxy-L-lyxo-hex-1-enofuranose (ent-6).

Ent-6 was prepared on 0.77 mmol scale in 61% yield from ent-3 as described above for the D-antipode. For ent-6: $[\alpha]_D{}^{23} = +212.6°$ (c. 1.03, CHCl$_3$); MS m/e 23 (relative intensity) 212 (13.5), 183 (100), 144 (10.6), 128 (17.8), 127 (14.8), 111 (70.5), 84(30.4) 83 (39.2), 69 (30.7), 55(89.1). Anal. Calcd for $C_{11}H_{16}O_4$: C, 62.25; H, 7.60. Found: C, 62.50; H, 7.41.

1,4 -Anhydro-3 -0-benzyl-5,6 -cyclopentyl idene-2 -deoxy-D-lyxo-hex-1-enofuranose (7).

A solution of furanose glycal 6 (64 rag, 0.30 mmol) in THF (2 mL) at 0° C. was treated with NaIl (60% in oil, 18 rag, 0.45 mmol, 1.5 eq), benzyl bromide (45 µL, 65 mg, 0.38 mmol, 1.27 eq), and tetrabutyl ammonium iodide (5 mg). After warming to room temperature and stirring for 8 hrs., the mixture was diluted with water and extracted three times with EtOAc. Pooled extracts were washed with water, brine, dried (MgSO$_4$), and evaporated. Chromatography over silica gel (eluted with 5% EtOAc in hexanes) gave 78 mg (86%) of (7) as a clear colorless oil $[\alpha]^{23}{}_D = -2.33.4°$ (c. 1.06, CHC13); IR (CHC13) 3010, 2985, 2880, 1615, 1460, 1360, 1340, 1155, 1110, 1080, 1050, 975 cm$^{-1}$; $^1$H NMR (CDCl$_3$, 250 MHz) δ7.29-7.37 (m, 5H, ArH), 6.61 (dd, 1H, J=1.0, 2.7 Hz, Hi), 5.23 (t, 1H, J=2.7 Hz, H2), 4.65 (ddd, 1H, J=1.0, 2.7, 3.3 Hz, H3), 4.53 (s, 2H, ROCH$_2$Ph), 4.47 (dd, 1H, J=3.3, 6.1 Hz, H4), 4.15 (ddd, 1H, J=5.9, 6.1, 6.9 Hz, H5), 3.93 (dd, 1H, J=6.9, 8.4 Hz, H6), 3.79 (dd, 1H, J=5.9, 8.4 Hz, H6'), 1.64-1.90 (m, 16H).

1,4-Anhydro-3-O,benzyl-5,6-cyclopentylidene-2-deoxy-L-lyxo-hex-1-enofuranose (ent-7).

This compound was prepared on the 0.26 mmol scale in 94% yield from hydroxy glycal ent-6 as described above for the D-antipode (7). $[\alpha]_D{}^{22} = +220.9°$ (c. 0.83, CHCl$_3$). Anal. Calcd for $C_{18}H_{22}O_4$: C, 71.50; H, 7.33. Found: C, 71.45; H, 7.09.

b. Formation of Resorcinol Derivative and Protected 2,4-Dihydroxybenzoic Acid Derivatives. 5,7-Dihydroxy-2,2-dimethyl-4H-1,3-benzodioxin-4-one (9).

To an ice-cold suspension of 2,4,6-trihydroxybenzoic acid monohydrate, (8) (5.0 g, 27 mmol) in trifluoroacetic acid (40 mL) was added trifluoroacetic anhydride (25 mL) and acetone (5 mL). The mixture was warmed slowly to room temperature and then stirred for 24 hrs. The slightly yellow homogeneous mixture was then concentrated on the rotary evaporator, poured into a saturated solution of aqueous NaHCO$_3$, and extracted with three portions of ethyl acetate. Pooled extracts were washed with water, brine, dried (MgSO$_4$), and concentrated to leave yellow solids. Chromatography over silica using 35% EtOAc in hexanes as the eluant left 1.88 g (34%) of white solids. m.p. 203°-204° C. IR (CHCl$_3$) 3200, 3020, 1680, 1640, 1595, 1490, 1275, 1165, 1100 cm$^{-1}$; $^1$H NMR (d$_6$-acetone, 250 MHz) δ10.44 (br s, 1H, o-OH), 6.06 (d, 1H, J=2.2 Hz, ArH), 5.98 (d, 1H, J=2.2 Hz, ArH), 3.02 (br s, 1H, p-OH), 1.70 (s, 6H, CH$_3$). Anal. Calcd for $C_8H_{10}O_5$: C, 57.14; H, 4.80. Found: C, 56.87; H, 4.63.

7-Benzyloxy-2,2-dimethyl-5-hydroxy-4H-1,3-benzodioxin-4-one (10).

To a solution of diol (9) (1.88 g, 8.95 mmol) and benzyl alcohol (960 µL, 1.01 g, 9.40 mmol, 1.05 eq) in THF (45 mL) at 0° C. was added triphenyl phosphine (2.48 g, 9.40 mmol, 1.05 eq) and DIAD (1.86 mL, 1.90 g, 9.40 mmol, 1.05 eq) and the mixture was warmed to room temperature over 2 hrs. The solution was then diluted with EtOAc, washed thrice with water, brine, dried (MgSO$_4$), concentrated, and chromatographed over silica (eluted with 10% EtOAc-hexanes) to give 2.48 g (92%) of (10) as white solids. m.p. 80° C. IR (CHCl$_3$) 3200, 3020, 1685, 1640, 1585, 1500, 1275, 100, 1160, 1100 cm$^{-1}$; 1H NMR (CDCl$_3$, 250 MHz) δ10.46 (s, 1H, o-OH), 7.39-7.42 (m, 5H, ArH), 6.24 (d, 1H, J=2.2 Hz, ArH), 6.09 (d, 1H, J=2.2 Hz, ArH), 5.07 (s, 2H, OCH$_2$Ph), 1.74 (s, 6H, CH$_3$). Anal. Calcd for $C_{17}H_{16}O_5$: C, 67.99; H, 5.37. Found: C, 67.77; H, 5.39.

7-Benzyloxy-2,2-dimethyl-5-trifluoromethanesulfonyl-4H-1,3-benzodioxin-4-one (11).

A solution of alcohol (10) (2.4 g, 8.0 mmol) in pyridine (40 mL) at 0° C. was treated dropwise with trifluoromethanesulfonic anhydride (1.48 mL, 2.48 g, 8.8 mmol, 1.1 eq) and the mixture was maintained at 0° C. for 12 hrs. The solution was then concentrated on the rotary evaporator, diluted with 4:1 Et20-EtOAc (200 mL), washed thrice with water, brine, dried (MgSO$_4$), and then evaporated to leave a dark oil. Chromatography over silica gel (eluted with 12.5% EtOAc-hexanes) gave 2.94 g (85%) white solids. m.p. 86°-88° C. IR (CHCl$_3$) 3020, 1690, 1630, 1575, 1435, 1385, 1160, 1060 cm$^{-1}$; $^1$H NMR (CDCl$_3$, 250 MHz) δ 7.42-7.50 (m, 5H, ArH), 6.61 (d, 1H, J=2.3 Hz), 6.57 (d, 1H, J=2.3 Hz), 5.11 (s, 2H, OCH$_2$Ph), 1.75 (s, 6H, CH$_3$). Anal. Calcd for C$_{18}$H$_{15}$F$_3$O$_7$S: C, 50.00, H, 3.50. Found: C, 50.19; H, 3.57.

7-Benzyloxy-2,2-dimethyl-5- ( 1-heptyn-1-yl ) -4H-1,3-benzodioxin-4-one (12).

A solution of triflate (11) (2.78 g, 6.4 mmol), 1-heptyne (1.18 mL, 864 mg, 9.0 mmol, 1.4 eq), and bis-(triphenylphosphine)-palladium (II) chloride (105 mg, 0.150 mmol, 0.02 eq) in DMF-Et$_3$N (5:1, 20 mL) was heated to 90° C. for 12 hrs. The solution was then cooled, diluted with Et$_2$O (200 mL), washed thrice with water, brine, dried (MgSO$_4$), and concentrated to leave a yellow oil. Chromatography over silica gel (eluted with 12% EtOAc-hexanes) gave 2.11 g (87%) of pale yellow solids. An analytical sample recrystallized from EtOAc-hexanes gave m.p. 104° C.

IR (CHCl$_3$) 3010, 3000, 2930, 2230, 1725, 1600, 1570, 1280, 1170 cm$^{-1}$; $^1$H NMR (CDCl$_3$, 250 MHz) δ7.36-7.43 (m, 5H, ArH), 6.84 (d, 1H, J=2.5 Hz, ArH), 6.45 (d, 1H, J=2.5 Hz, ArH), 5.08 (s, 2H, OCH$_2$Ph), 2.52 (br t, 2H, J=7.0 Hz, CH$_2$), 1.70 (s, 6H, CH$_3$), 1.32-1.68 (m, 6H), 0.93 (t, 3H, J=7.2 Hz, CH$_3$). Anal. Calcd for C$_{24}$H$_{26}$O$_4$: C, 76.17; H, 6.92. Found: C, 76.04; H, 6.95.

2,2-Dimethyl-5- ( 1-heptyl ) -7-hydroxy-4H-1,3-benzodioxin-4-one (13).

Compound (12) (500 mg, 1.32 mmol) was hydrogenated over Pd(OH)$_2$ (20%, 95 mg, ca. 0.1 eq.) in EtOH (15 mL) at atmospheric pressure for 12 hrs. Filtration through Celite TM and concentration left 387 mg (100%) of white solids. m.p. 100°-102° C. IR (CHCl$_3$) 3100-3400, 3020, 2930, 1715, 1615, 1590, 1450, 1390, 1295, 1170, 1050 cm$^{-1}$; $^1$H NMR (CDCl$_3$, 250 MHz) δ6.42 (d, 1H, J=2.4 HZ, ArH), 6.27 (d, 1H, J=2.4 Hz, ArH), 5.50 (br s, 1H, OH), 3.04 (br t 2H, J=7.7 Hz), 1.69 (s, 6H, CH$_3$), 1.20-1.65 (m, 10H), 0.88 (t, 3H, J=7.2 Hz, CH$_3$).

5-Heptyl-resorcinol (14).

Compound (13) (383 mg, 1.31 mmol) in DMSO (6 mL) was treated with 48% aqueous KOH (1.5 mL) and the mixture was heated to 115° C. under a gentle stream of N$_2$ for 4.5 hrs. Upon cooling, the solution was diluted with water, acidified (10% HCl), and extracted three times with EtOAc. Pooled extracts were washed with three portions of water, with brine, dried (MgSO$_4$), and concentrated. Chromatography of the resulting yellow oil over silica gel (eluted with 17-20% EtOAc-hexanes) gave 270 mg (99%) of the known 5-heptyl-resorcinol as a pale yellow oil.

Benzyl 2,4-dihydroxy-6-(1-heptyl)-benzoate (15). To a solution of compound (13) (200 mg, 0.685 mmol) in THF (10 mL) was added BnOLi (0.5 M in THF, 6.8 mL, 3.4 mmol, 5 eq) and the mixture was heated to reflux for 65 hrs. Upon cooling, the mixture was diluted with water and extracted with EtOAc. Pooled extracts were washed with aqueous HCl (10%), twice with water, with brine, and then dried (MgSO$_4$). Concentration and chromatography over silica gel (using 8% EtOAc-hexanes as eluant) gave 214 mg (91%) of (15) as slightly pale solids. An analytical sample crystallized from a minimum of EtOAc in hexanes gave m.p. 104° C. IR (CHCl$_3$) 3580, 3030, 2980, 2930, 1655, 1620, 1450, 1395, 1320, 1270, 1175, 1110 cm$^{-1}$; $^1$H NMR (CDCl$_{13}$, 250 MHz) δ11.79 (s, 1H, o-OH), 7.38-7.47 (m, 5H, ArH), 6.29 (d, 1H, J=2.6 Hz, ArH), 6.21 (d, 1H, J=2.6 Hz, ArH), 5.36 (s, 2H, OCH$_2$Ph), 5.34 (br s, 1H, p-OH), 2.76 (br t, 2H, J=7.9 Hz), 1.07-1.47 (m, 10H), 0.88 (t, 3H, J=7.2 Hz, CH$_3$). Anal. Calcd for C$_{21}$H$_{26}$O$_4$: C, 73.66; H, 7.65. Found: C, 73.58; H, 7.63.

⊕-Trimethylsilylethyl 4-benzyloxy-6-(1-heptyn-1-yl)-2-hydroxy-benzoate (17).

Compound (12) (250 mg, 0,661 mmol) in DMSO (3 mL) was treated with 48% aqueous KOH (0.5 mL) and the mixture was heated at 60° C. for 30 mins. Upon cooling the solution was acidified (10% HCl), extracted three times with EtOAc, and these extracts were washed with water, brine, and dried over Na$_2$SO$_4$. Filtration and concentration left 248 mg of the crude acid (16) as yellow solids. IR (CHCl$_3$) 3200-3340, 3030, 2960, 2930, 2230, 1680, 1600, 1575, 1360, 1260, 1215, 1180, 1030 cm$^{-1}$; $^1$H NMR (CDCl$_3$, 250 MHz) δ12.26 (s, 1H, o-OH), 7.34-7.42 (m, 5H, ArH), 6.70 (d, 1H, J=2.6 Hz, ArH), 6.56 (d, 1H, J=2.6 Hz, ArH), 5.11 (s, 2H, OCH$_2$Ph), 2.56 (br t, 2H, J=7.1 Hz, CH$_2$), 1.61-1.73 (m,2H), 1.27-1.50 (m, 4H), 0.94 (t, 3H, 7.1 Hz, CH$_3$). The foregoing crude acid and 2-trimethylsilyl ethanol (0.95 mL, 782 mg, 6.61 mmol, 10 eq) were taken up in CH$_2$Cl$_2$ (6 mL) and treated at room temperature with 4-DMAP (89 mg, 0.723 mmol, 1.1 eq) and EDCI (279 mg, 1.46 mmol, 2.2 eq). The mixture was stirred for 5 hrs., then diluted with EtOAc, washed with aqueous NH$_4$Cl, twice with water, brine, and dried over MgSO$_4$. Concentration and chromatography over silica gel (eluted with 2% EtOAc-hexanes) left 254 mg (88%) of (17) as a clear colorless oil. IR (CHCl$_3$) 3020, 2940, 2840, 2220, 1650, 1600, 1570, 1330, 1265, 1210, 1170, 1030, 8040 cm$^{-1}$; $^1$H NMR (CDCl$_3$, 250 MHz) δ 11.77 (s, 1H, o-OH), 7.34-7.43 (m, 5H, ArH), 6.71 (d, 1H, J=2.6 Hz, ArH), 6.50 (d, 1H, J=2.6 Hz, ArH), 5.07 (s, 2H, OCH$_2$Ph), 4.45 (m, 2H, CO$_2$CH$_2$), 2.44 (br t, 2H, J=7.1 Hz, CH$_2$), 1.55-1.69 (m, 2H), 1.30-1.51 (m, 4H), 1.20 (m, 2H, CH$_2$TMS), 0.94 (t, 3H, 7.0 Hz, CH$_3$), 0.10 (s, 9H, TMS). Anal. Calcd for C$_{26}$H$_{34}$O$_4$Si: C, 71.19; H, 7.81. Found: C, 71.08; H, 7.58.

c. Assembly of Synthesized Intermediates into KS-501, ent-KS-501, KS-502 and ent-KS-502.

[3'-Benzyloxy-6'-(carboxy-β-trimethylsilylethyl)-5'-(1-heptyn-1-yl)phenyl]-2-O-benzyl-5,6-cyclopentylidene-D-galactofuranoside (19).

An ice-cold solution of glycal (7) (96 mg, 0.32 mmol) in CH$_2$Cl$_2$ (4 mL) was treated dropwise with 2,2-dimethyldioxirane (0.08 M in acetone, 4 mL, 1 eq). After 10 minutes the solvent was evaporated under a gentle stream of dry N$_2$ and the flask was then evacuated under reduced pressure for 10 mins. The resulting crude 1α,2α anhydrosugar (18) was taken up in dry acetone (5 mL) and added to a refluxing solution of aryl alcohol (17) (139 mg, 0.32 mmol), K$_2$CO$_3$ (440 mg, 3.2 mmol, 10 eq), and 18-crown-6 (10 mg) in acetone (5 mL). After refluxing for 8 hrs. the solution was cooled, diluted with saturated aqueous NH$_4$Cl, and extracted twice with EtOAc. Combined extracts were washed with water, brine, dried (MgSO$_4$), evaporated, and chromatographed over silica gel (eluted with 18% EtOAc in hexanes) to give 195 mg (81%) of (19) as a clear colorless oil. [α]$^{20}_D$= −48.6° (c. 0.96, CHCl$_3$); IR (CHCl$_3$) 3230-3500, 3010, 2980, 2880, 1720, 1600, 1500, 1460, 1275, 1175, 1110, 1035, 850 cm$^{-1}$; $^1$H NMR (CDCl$_3$, 490 MHz) δ7.28–7,433 (m, 10H, ArH), 6.77 (d, 1H, J=2.3 Hz, ArH), 6.73 (d, 1H, J=2.3 Hz, ArH), 5.55 (s, 1H, HI) 5.05 (s, 2H, ArOCH$_2$Ph), 4.74 (d, 1H, J=12.0 Hz, ROCH$_2$Ph), 4.56 (d, 1H, J=12.0 Hz, OCH$_2$Ph), 4.38 (br d, 1H, J=9.8 Hz, H2), 4.23–4.33 (overlapping m, 3H), 4.13 (ddd, 1H, J =2.1, 6.8, 7.8 Hz, H5), 3.99 (m, 1H, H3 ), 3.97 (dd, 1H, J=6.8, 8.1 Hz, H6), 3.92 (dd, 1H, J=7.8, 8.1 Hz, H6'), 3.68 (d, 1H, 9.8 Hz, OH), 2.37 (t, 2H, J=7.1 Hz, CH$_2$), 1.32–1.85 (m, 14 H) , 1.08 (t, 2H, J=8.8 Hz, TMSCH$_2$R), 0.93 (t, 3H, J=7.2 Hz, CH$_3$), 0.11 (s, 9H, TMS).

[3 '-Benzyloxy-6'- ( carboxy-β-trimethylsilylethyl)-5'-(1-heptyn-1-yl) phenyl]-2-O-benzyl-5,6-cyclopentylidene-L-galactofuranoside (ent-19 ).

This compound was prepared on the 0.28 mmol scale in 82% yield from L-glycal ent-7 as described above for the D-antipode (19). [α]$_D^{22}$= +51.3° (c. 0.90, CHCl$_3$); FABLRMS (NOBA+NaI) m/e (relative intensity) 780(22.7), 779 (40.0), 729 (17.0) , 411 (58.2) , 410 (56.0), 320 (25.6), 319 (100); FABHRMS Calcd for C$_{44}$H$_{56}$O$_9$·SiNa 779.3591, found 779.3599. Anal. Calcd for C$_{44}$H$_{56}$O$_9$Si: C, 69.81; H, 7.46. Found: C, 69.66; H, 7.19.

[3'-Benzyloxy-6'-(carboxy-β-trimethylsilylethyl)-540-(1-heptyn-1-yl)phenyl]-2,3-di-O-benzyl-5,6-cyclopentylidene-D-galactofuranoside (20).

To an ice-cold solution of hydroxy aryl glycoside (19) (162 mg, 0.21 mmol) in THF (4 mL) was added NaII (60% in oil, 21 rag, 0.54 mmol, 2.5 eq), benzyl bromide (33 μL, 47 rag, .28 mmol, 1.3 eq), and tetrabutyl ammonium iodide (10 mg), and the solution was allowed to warm to room temperature and was then stirred for 6 hrs. The reaction was then diluted with saturated aqueous NH$_4$Cl, extracted twice with EtOAc, extracts were washed with water, brine, dried (MgSO$_4$), and evaporated. Chromatography over silica gel (eluted with 10% EtOAc in hexanes) gave 164 mg (90%) of (20) as a clear colorless oil [α]$_D^{26}$= −54.9° (c. 0.79, CHCl$_3$); IR (CHCl$_3$), 3010, 2980, 2890, 1720, 1600, 1310, 1280, 1175, 1115 cm$^{-1}$; $^1$H NMR (CDCl$_3$, 490 MHz) a 7.28–7.43 (m, 15 H, ArH), 6.79 (d, 1H, J=2.1 Hz, ArH), 6.74 (d, 1H, J=2.1 Hz, ArH), 5.62 (s, 1H, HI), 5.04 (s, 2H, ArOCH$_2$Ph), 4.64 (d, 1H, J=11.8 Hz, ROCH$_2$Ph), 4.59 (d, 1H, J=11.8 Hz, ROCH$_2$Ph) , 4.59 (d, 1H, J=11.8 Hz, ROCH$_2$Ph), 4.51 (d, 1H, J=11.8 Hz, ROCH$_2$Ph), 4.34 (m, 2H, ArCO$_2$CH$_2$R), 4.28 (m, 1H, H2), 4.21 (dd, J=6.0, 6.6 Hz, H4) 4.18 (ddd, J=6.0, 6.6, 6.6 Hz, H5), 4.00 (dd, J=3.4, 6,6 Hz, H3), 3.86 (d, 2H, J=6.6 Hz, H6, H6'), 2.38 (t, 2H, J=7.2 Hz, CH$_2$), 1.33–1.87 (m, 14H), 1.09 (m, 2H, TMSCH$_2$R), 0.93 (t, 3H, J=7.1 HZ, CH$_3$), 0.02 (s, 9H, TMS).

[3 '-Benzyloxy-6'- (carboxy-β-trimethylsilylethyl) -5'(1-heptyn-1-yl )phenyl]-2,3-di-O-benzyl-5,6-cyclopentylidene-L-galactofuranoside (ent-20).

This compound was prepared on the 0.28 mmol scale in 98% yield from hydroxy aryl glycoside ent-19 as described above for the D-antipode (20). [α]$_D^{23}$= +65.5° (0.92, CHCl$_3$); FABLRMS (NOBA+NaI) m/e (relative intensity) 870 (68.2), 869 (95.5), 819 (26.2), 411 (65.8), 321 (100), FABHRMS calcd for C$_{51}$H$_{62}$O$_9$SiNa 869. 4061, found 869. 4051. Anal. Calcd for C$_{51}$H$_{62}$O$_9$Si: C, 72.31; H, 7.38. Found: C, 72.09; H, 7.06.

[3'-Benzyloxy-6'-carboxy-5'-(1-heptyn-1-yl)phenyl]-2,3-di-O-benzyl-5,6-cyclopentylidene-D-galactofuranoside (21).

A solution of aryl glycoside (20) (160 mg, 0.19 mmol) in THF (5 mL) was treated at room temperature with TBAF (1.0M in THF, 567 μL, 0.57 mmol, 3 eq) and the mixture was allowed to stir for 4 hrs. Saturated aqueous NH$_4$Cl was then added and the mixture was diluted with EtOAc. This solution was washed with cold dilute HCl (0.5%), water, brine, and dried over Na$_2$SO$_4$. Evaporation and chromatography over silica gel (eluted with 0.25% AcOH in 25% EtOAc in hexanes) gave 135 mg (96%) of acid (21) as a clear colorless oil. [α]$_D^{26}$= −66.2° (c. 1.35, CHCl3); IR (CHCl$_3$), 3220–3600, 3010, 2980, 2970, 2890, 1730, 1600, 1580, 1455, 1340, 1325, 1175, 1110 cm$^{-1}$; $^1$H NMR (CDCl$_3$, 490 MHz) δ7.26–7.41 (m, 15H, ArH), 6.80 (d, 1H, J=2.3 Hz, ArH), 6.74 (d, 1H, J=2.3 Hz, ArH), 5.72 (s, 1H, H1), 5.04 (s, 2H, ArOCH$_2$Ph), 4.58 (d, 1H, J=12.1 Hz, ROCH$_2$Ph), 4.54 (d, 1H, J=11.8 Hz, ROCH$_2$Ph), 4.51 (d, 1H, J=11.8 Hz, ROCH$_2$Ph), 4.49 (d, 1H, J=12.1 Hz, ROCH$_2$Ph), 4.24 (m, 1H, H2), 4.22 (dd, 1H, J=4.6, 5.9 Hz, H4) 4.14 (ddd, J=5.9, 6.3, 6.3 Hz, H5), 3.91 (dd, J=1.8, 4.6 Hz, H3), 3.76 (overlapping m, 2H, H6, H6'), 2.40 (t, 2H, J=7.2 Hz, CH$_2$), 1.30–1.81 (m, 14H), 0.89 (t, 3H, J=7.2 Hz, CH$_3$)

[3'-Benzyloxy-6'-carboxy-5'-(1-heptyn-1-yl) phenyl]-2,3-di-O-benzyl-5,6-cyclopentylidene-L-galactofuranoside (ent-21).

This compound was prepared on the 0,092 mmol scale in 92% yield from aryl glycoside ent-20 as described above for the D-antipode ( 21 ). [α]$_D^{23}$= +68.1° (c. 1.07, CHCl$_{13}$); FABLRMS (NOBA+NaI) m/e (relative intensity) 770 (11.4), 769 (25.3), 409 (23.7), 321 (50.6), 307 (58.4), 289 (41.5), 217 (31.9), 181 (100); FABHRMS calcd for C$_{46}$H$_{50}$O$_9$Na 769.3352, found 769.3380.

[3'-Benzyloxy-6'-(carboxy-(5''-(1-heptyl)-3''-hydroxy)phenyl)-5''-(1-heptyn-1-yl)phenyl]-2,3-di-O-benzyl-D-galactofuranoside (22).

A solution of acid (21) (30 rag, 0.04 mmol) and 5-heptyl resorcinol (83 rag, 0.40 mmol, 10 eq) in CH$_2$Cl$_2$ (2 mL) was treated at room temperature with 4-DMAP (6.3 rag, 0. 052 mmol, 1.3 eq) and EDCI (33.0 mg, 0.17 mmol, 4.3 eq). After 6 hrs. the solution was diluted with saturated aqueous NH$_4$Cl and extracted twice with EtOAc. Extracts were then washed with water, brine, dried (MgSO$_4$), and evaporated. Partial purification was performed by passage through a short column of silica gel (eluted with 15% EtOAc in hexanes) to provide recovered 5-heptyl resorcinol (67 mg) and impure esterified arylfuranoside (18 mg). This material was stirred for 30 mins. at room temperature in TsOH-MeOH (0.025 M, 4 mL). The solution was then diluted with aqueous NaHCO$_3$ and EtOAc, the organic layer was washed with water, brine and then dried over MgSO$_4$. Evaporation and chromatography over silica gel (eluted with 50% EtOAc in hexanes) gave 14.4 mg (41% from acid (21)) of pure (22) as a clear colorless oil. [α]$_D^{26}$= −69.7° (c. 1.03, CHCl$_3$); IR (CHCl$_3$), 3150–3600, 3010, 2980, 2880, 1745, 1600, 1455, 1260, 1170, 1135, 1035 cm$^{-1}$; $^1$H NMR (CDCl$_3$, 490 MHz) δ7.24–7.40 (m, 15H, ArH), 6.77 (d, 1H, J=2.2 Hz, ArH), 6.63 (d, 1H, J=2.2 Hz, ArH), 6.59 (br t, 1H, J= <2Hz, ArH), 6.50 (overlapping m 2H, ArH), 5.63 (s, 1H, Hi), 5.03 (s, 2H, ArOCH$_2$Ph), 4.56 (d, 1H, J=11.9 Hz, ROCH$_2$Ph), 4.55 (d, 1H, J=11.7 Hz, ROCH$_2$Ph), 4.49 (d, 1H, J-11.7 Hz, ROCH$_2$Ph), 4.48 (d, 1H, J=11.9 Hz, ROCH$_2$Ph) , 4.28–4.30 (overlapping m 2H, H2, H4), 4.11 (dd, 1H, J=2.9, 6.7 Hz, H3), 3.73 (br ddd, J=6.7, 5.0, 5.0 Hz, H5), 3.61 (d, 2H, J=5.0 Hz, H6, H6'), 2.49 (t, 2H, J=7.8 Hz, ArCH$_2$R) , 2.39 (t, 2H, J=7.2 Hz, CH$_2$), 1.23–1.64 (m, 16H), 0.84–0.87 (overlapping t, 6H, CH$_3$). [3'-Benzyloxy-6'-(carboxy-(5''-(1- heptyl)-3"-hydroxy)phenyl)-5'-(1-heptyn-1-yl) phenyl]-2,3-di-O-benzyl-L-galactofuranoside ( ent-22 ) .

This compound was prepared on the 0.04 mmol scale in 49% yield from acid ent-21 as described above for the D-antipode (22). $[\alpha]_D^{22} = +69.1°$ (c. 0.65, CHCl$_3$); FABLRMS (NOBA+NaI) m/e (relative intensity) 893 (4.9), 663 (4.9), 5.29 (13.4), 321 (100), FABHRMS calcd for C$_{54}$H$_{62}$O$_{10}$Na 893.4241, found 893.4268. Anal. Calcd for C54H62010: C, 74.46; H, 7.17. Found: C,74.70; H, 6.98.

[3'-Benzyloxy-6'-(carboxy-(4"-carboxybenzyl-5"-(1-heptyl)-3"-hydroxy)phenyl)-5'-(1-heptyn-1-yl) phenyl]-2,3-di-O-benzyl-D- galactofuranoside (23).

A solution of acid (21) (135 rag, 0.18 mmol) and aryl alcohol (15) (62 mg, 0.18 retool, 1 eq) in CH$_2$Cl$_2$ (5 mL) was treated at room temperature with 4-DMAP (24 mg, 0.20 mmol, 1.1 eq) and EDCI (69 rag, 0.36 mmol, 2 eq). After 4 hrs. the solution was diluted with saturated aqueous NH$_4$Cl and extracted twice with EtOAc. Extracts were then washed with water, brine, dried (MgSO$_4$), and evaporated. Partial purification was performed by passage through a short column of silica gel (eluted with 10% EtOAc in hexanes) to provide the desired esterified arylfuranoside contaminated with starting aryl alcohol (15) (190 mg, ca. 2.2:1 by $^1$H NMR). This material was stirred for 30 min at room temperature in TsOH-MeOH (0.025 M, 10 mL). The solution was then diluted with aqueous NaHCO$_3$ and EtOAc, the organic layer was washed with water, brine and then dried over MgSO$_4$. Evaporation and chromatography over silica gel (eluted with 40% EtOAc in hexanes) gave 123 mg (68% from acid (21)) of pure (23) as a clear colorless oil. $[\alpha]_D^{26} = -60.4°$ (c 1,08, CHCl$_3$); IR (CHCl$_3$), 3300–3600, 3010, 2980, 2970, 2885, 1750, 1715, 1660, 1600, 1460, 1365, 1320, 1250, 1145, 1035 cm$^{-1}$; $^1$H NMR (CDCl$_3$, 490 MHz) δ 11.39 (s, 1H, o-OH), 7.22–7.43 (m, 20H, ArH), 6.81 (d, 1H, J=2.3 Hz, ArH), 6.77 (d, 1H, J=2.2 Hz, ArH), 6.66 (d, 1H, J=2.2 Hz, ArH), 6.58 (d, 1H, J=2.3 Hz, ArH), 5.61 (s, 1H, HI), 5.37 (s, 2H, ArCO$_2$CH$_2$Ph), 5.04 (s, 2H, ArOCH$_2$Ph), 4.58 (d, 1H, J=12.0 Hz, ROCH$_2$Ph), 4.51 (d, 1H, J=11.7 Hz, ROCH$_2$Ph), 4.47 (d, 1H, J=12.0 Hz, ROCH$_2$Ph), 4.46 (d, 1H, J=11.7 Hz, ROCH$_2$Ph), 4.25 (m, 1H, H2), 4.24 (dd, 1H, J=3.6, 6.5 Hz, H4), 4.09 (dd, 1H, J=2.9, 6.5 Hz, H3), 3.70 (m, 1H, H5), 3.58–3.60 (overlapping m 2H, H6, H6'), 2.75 (t, 2H, J=8.0 Hz, ArCH2R), 2.37 (t, 2H, J=7.2 Hz, CH$_2$), 1.00–1.57 (m, 16H), 0.82–0.86 (overlapping t, 6H, CH$_3$).

[3'-Benzyloxy-6'-(carboxy-(4"-carboxybenzyl-5"-(1-heptyl )-3"-hydroxy) phenyl)-5'- (1-heptyn-1-yl) phenyl]-2,3-di-O-benzyl-L-galactofuranoside (ent-23) . This compound was prepared on the 0.04 mmol scale in 69% yield from acid ent-21 as described above for the D-antipode (23). $[\alpha]_D^{22} = +58.0°$ (c 1.07, CHCl$_3$); FABLRMS (NOBA+NaI) m/e (relative intensity) 1027 (2.6), 663 (6.3), 411 (6.24), 321 (100); FABHRMS calcd for C$_{62}$H$_{68}$O$_2$Na 1027.4668, found 1027.4668. Anal. Calcd for C62H68012: C, 74.08; H, 6.82. Found: C,73.79; H, 6.56.

KS 501 (1).

Compound (22) (14 mg, 0,016 mmol) was hydrogenated over 10% Pd/C (15 mg) under 1 atm of H$_2$ in EtOH (3 mL) for 36 hrs. The mixture was filtered, evaporated, and passed through a short pad of silica gel (eluted with 15% MeOH in CHCl$_3$ to leave 10.4 mg (100%) of pure (1) as a clear oil that solidified on standing. $[\alpha]_D^{23} = +54.3°$ (c. 0.67, MeOH$_3$), (lit $[\alpha]_D^{23} = -53°$ (c. 0.3, MeOH$_3$)). This product was identical by tlc mobility, UV, and $^1$H NMR spectra to the natural material.

ent-KS 501 (ent-(1)).

Compound ent-(22) (17 mg, 0.02 mmol) was hydrogenated over 10% Pd/C (20 mg) under 1 atm of H$_2$ in EtOH (4 mL) for 36 hrs. The mixture was filtered, evaporated, and passed through a short pad of silica gel (eluted with 15% MeOH in CHCl$_3$) to leave 10.4 mg (88%) of pure ent-(1) as a clear oil that solidified on standing. $[\alpha]_D^{23} = +53.5°$ (c. 0.68, MeOH$_3$). This product was identical by tlc mobility, UV, and $^1$H NMR spectra to the natural isomer.

KS 502 (2).

Compound (23) (120 mg, 0.12 mmol) was hydrogenated over 10% Pd/C (100 mg) under 1 atm of H$_2$ in EtOH (10 mL) for 14 hrs. The mixture was filtered, evaporated, and passed through a short pad of LiChroprep® RP-18 (eluted with MeOH) to leave 77 mg (100%) of pure (2) as a clear oil that solidified on standing. $[\alpha]_D^{22} = -42.8°$ (c. 0.54, MeOH).. (lit $[\alpha]_D^{23} = -45°$ (c. 0.3, MeOH)). This product was identical by tlc mobility, UV, and $^1$H NMR spectra to the natural material.

ent-KS 502 (ent-(2)).

Compound ent-(23) (19 mg, 0.019 mmol) was hydrogenated over 10% Pd/C (15 mg) under 1 atm of H$_2$ in EtOH (3 mL) for 24 hrs. The mixture was filtered, evaporated, and passed through a short pad of LiChroprep®RP-18 (eluted with MeOH) to leave 13 mg (100%) of pure ent-(2) as a clear oil that solidified on standing. $[\alpha]_D^{22} = +42.0°$ (c. 0.40, MeOH). This product was identical by tlc mobility, UV, and $^1$H NMR spectra to the natural isomer.

Equivalents

Those skilled in the art will recognize or be able to ascertain using no more than routine experimentation, many equivalents to the specific embodiments of the invention described herein. Such equivalents are intended to be encompassed in the scope of the following claims.

I claim:

1. A method for producing the compound

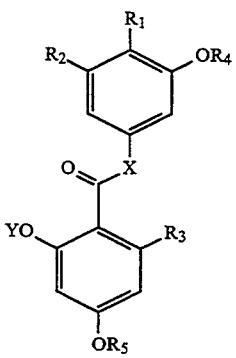

wherein:
R$_1$ is selected from the group consisting of H, CO$_2$H, CO$_2$-lower alkyl, and CO$_2$-benzyl;
R$_2$ and R$_3$ are independently H or a C$_1$–C$_{20}$ saturated or unsaturated straight- or branched-chain alkyl group;
R$_4$ and R$_5$ are independently selected from the group consisting of H, Si-alkyl, Si-alkoxy, Si-aryl, and benzyl;

X is either oxygen or sulfur; and
Y is a glycoside; said method comprising the steps:
a) initially combining a derivative of Y, wherein said derivative is a sugar glycal, with a first 2,4-dihydroxybenzoic acid derivative which has said $R_3$ and $R_5$ substituents, said initial combining occurring under conditions appropriate for covalent attachment of said sugar glycal to said first 2,4-dihydroxybenzoic acid derivative through an oxygen atom at the 2 position of said first 2,4-dihydroxybenzoic acid derivative, thereby producing an arylglycoside, and
b) subsequently combining the arylglycoside produced in step a) with an aryl compound which has said $R_1$, $R_2$ and $R_4$ substituents, said subsequent combining occurring under conditions appropriate for a covalent attachment reaction to occur through X between said arylglycoside and said aryl compound, thereby forming said compound.

2. The method of claim 1 wherein X is oxygen and Y selected from the group consisting of β-D-galactofuranoside, β-L-galactofuranoside, β-D-glucopyranoside, β-L-glucopyranoside, β-D-galactopyranoside and β-L-galactopyranoside.

3. The method of claim 2 wherein:
said aryl compound is a resorcinol derivative;
$R_1$ is H; and
said subsequent combining occurs through an esterification between the 3-position hydroxyl of said resorcinol derivative and the carboxylate group of said first 2,4-dihydroxybenzoic acid derivative such that an ester linkage is formed.

4. The method of claim 3 wherein the hydroxy positions of said sugar glycal have attached protective groups independently selected from the group consisting of H, alkyl, cycloalkyl, Si-alkyl, Si-alkoxy, Si-aryl, and benzyl.

5. The method of claim 4 wherein said sugar glycal is a furanose glycal with a monosubstituted or disubstituted dioxolane and wherein the substituents of said substituted dioxolane are independently selected from the group consisting of H, alkyl and cycloalkyl.

6. The method of claim 5 wherein said sugar glycal is either 1,4-anhydro-3-O-benzyl-5,6-cyclopentylidene-2-deoxy-D-!yxo-hex-1-enofuranose or 1,4-anhydro-3-O-benzyl-5,6-cyclopentylidene-2-deoxy-L-lyxo-hex-1-enofuranose.

7. The method of claim 6 wherein said sugar glycal is 1,4-anhydro-3-O-benzyl-5,6-cyclopentylidene-2-deoxy-D-!yx0-hex-1-enofuranose wherein said enofuranose is formed from D-talose.

8. The method of claim 6 wherein said sugar glycal is 1,4-anhydro-3-O-benzyl-5,6-cyclopentylidene-2-deoxy-L-lyxo-hex-1-enofuranose wherein said enofuranose is formed from L-talonic acid-g-lactone.

9. The method of claim 5 wherein said first 2,4-dihydroxybenzoic acid derivative is β-trimethylsilylethyl 4-benzyloxy-6-(1-heptyn-1-yl)-2-hydroxy-benzoate and said resorcinol derivative is 5-heptyl-resorcinol.

10. The method of claim 9 wherein said sugar glycal is either 1,4-anhydro-3-O-benzyl-5,6-cyclopentylidene-2-deoxy-D-lyxo-hex-1-enofuranose or 1,4-anhydro-3-O-benzyl-5,6-cyclopentylidene-2-deoxy-L-lyxo-hex-1-enofuranose.

11. The method of claim 10 wherein:
said sugar glycal is 1,4-anhydro-3-O-benzyl-5,6-cyclopentylidene-2-deoxy-D-lyxo-hex-1-enofuranose, wherein said enfuranose is formed from D-talose; and
the compound produced in said step b) is:

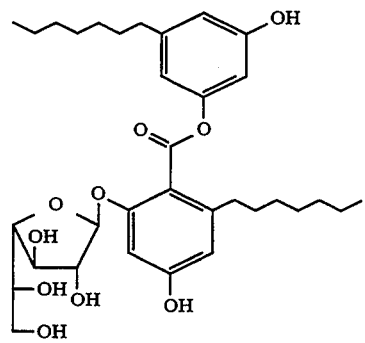

12. The method of claim 11 wherein said β-trimethylsilyl ethyl-4-benzyloxy-6-(1-heptyn-1-yl)-2-hydroxybenzoate and said 5-heptyl-resorcinol have each been synthesized from 2,4,6-trihydroxybenzoic acid.

13. The method of claim 10 wherein:
said sugar glycal is 1,4-anhydro-3-O-benzyl-5,6-cyclopentylidene-2-deoxy-L-lyxo-hex-1-enofuranose wherein said enofuranose is formed from L-talonic acid-g-lactone; and
the compound produced in said step b) is:

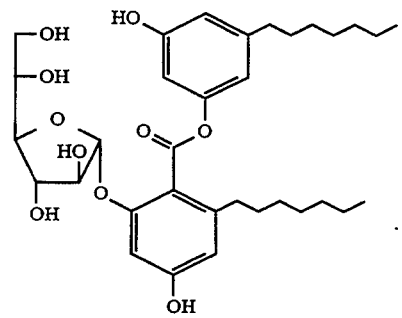

14. The method of claim 13 wherein said β-trimethylsilylethyl 4-benzyloxy-6-(1-hyptyn-1-yl)-2-hydroxybenzoate and said 5-heptyl-resorcinol have each been synthesized from 2,4,6-trihydroxybenzoic acid.

15. The method of claim 2 wherein:
said aryl compound is a second 2,4-dihydroxybenzoic acid derivative which has said $R_2$ and $R_4$ substituents and whose 4-position hydroxy is protected by a moiety selected from the group consisting of H, Si-alkyl, Si-alkoxy, Si-aryl, and benzyl;
$R_1$ is selected from the group consisting of $CO_2H$, $CO_2$-lower alkyl, and $CO_2$-benzyl; and
said subsequent combining occurs through an esterification between the 4-position oxygen of said second 2,4-dihydroxybenzoic acid derivative and the carboxylate group of said first 2,4-dihydroxybenzoic acid derivative such that an ester linkage is formed.

16. The method of claim 15 wherein the hydroxy positions of said sugar glycal have attached protective groups independently selected from the group consisting of H, Si-alkyl, Si-alkoxy, Si-aryl, and benzyl.

17. The method of claim 16 wherein said sugar glycal is a furanose glycal with a monosubstituted or disubstituted dioxolane and wherein the substituents of said substituted dioxolane are independently selected from the group consisting of H, alkyl, and cycloalkyl.

18. The method of claim 17 wherein said sugar glycal is either 1,4-anhydro-3-O-benzyl-5,6-cyclopentylidene-2-deoxy-D-lyxo-hex-1enofuranose or 1,4-anhydro-3-O-benzyl-5,6-cyclopentylidene-2-deoxy-L-! yxo-hex-1-enofuranose.

19. The method of claim 18 wherein said sugar glycal is 1,4-anhydro-3-O-benzyl-5,6-cyclopentylidene-2-deoxy-D-lyxo-hex-1-enofuranose wherein said enofuranose is formed from D-talose.

20. The method of claim 18 wherein said sugar glycal is 1,4-anhydro-3-O-benzyl-5,6-cyclopentylidene-2-deoxy-L-lyxo-hex-1-enofuranose wherein said enofuranose is formed from L-talonic acid-g-lactone.

21. The method of claim 17 wherein said first 2,4-dihydroxybenzoic acid derivative is $\beta$-trimethylsilylethyl 4-benzyloxy-6-(1-heptyn-1-yl)-2-hydroxybenzoate and said second 2,4-dihydroxybenzoic acid derivative is benzyl 2,4-dihydroxy6-(1-heptyl)-benzoate.

22. The method of claim 21 wherein said sugar glycal is either 1,4-anhydro-3-O-benzyl-5,6-cyclopentylidene-2-deoxy-D-lyxo-hex-1-enofuranose or 1,4-anhydro-3-O-benzyl-5,6-cyclopentylidene-2-deoxy-L-lyxo-hex-1-enofuranose.

23. The method of claim 22 wherein:
said sugar glycal is 1,4-anhydro-3-O-benzyl-5,6-cyclopentylidene-2-deoxy-D-lyxo-hex-1-enofuranose wherein said enofuranose is formed from D-talose; and
the compound produced in said step b) is

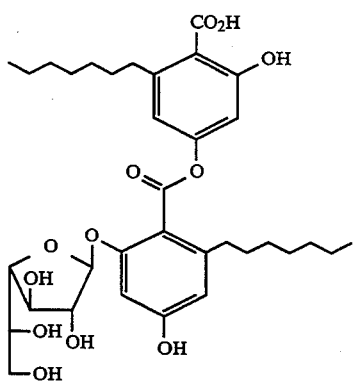

24. The method of claim 23 wherein said $\beta$-trimethylsilylethyl 4-benzyloxy-6-(1-heptyn-1-yl)-2-hydroxybenzoate and said benzyl 2,4-dihydroxy-6-(1-heptyl)-benzoate have each been synthesized from 2,4,6-trihydroxybenzoic acid.

25. The method of claim 22 wherein:
said sugar glycal is 1,4-anhydro-3-O-benzyl-5,6-cyclopentylidene-2-deoxy-L-lyxo-hex-1-enofuranose wherein said enofuranose is formed from L-talonic acid-g-lactone; and the compound produced in said step b) is:

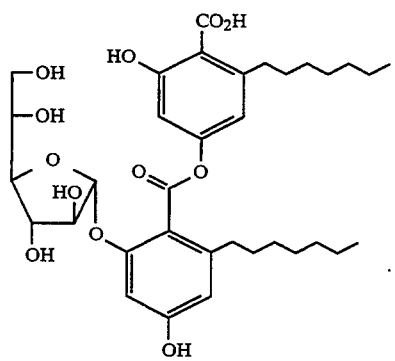

26. The method of claim 25 wherein said $\beta$-trimethylsilylethyl 4-benzyloxy-6-(1-heptyn-1-yl)-2-hydroxybenzoate and said benzyl 2,4-dihydroxy-6-(1-heptyl)-benzoate have each been synthesized from 2,4,6-trihydroxybenzoic acid.

27. The method of claim 1 wherein X is sulfur and Y is selected from the group consisting of $\beta$-D-galactofuranoside, $\beta$-L-galactofuranoside, $\beta$-D-glucopyranoside, $\beta$-L-glucopyranoside, $\beta$-D-galactopyranoside and $\beta$-L-galactopyranoside.

28. The method of claim 27 wherein the hydroxy positions of said sugar glycal have attached protective groups independently selected from the group consisting of H, alkyl, cyclalkyl, Si-alkyl, Si-alkoxy, Si-aryl, and benzyl.

29. The method of claim 28 wherein said sugar glycal is a furanose glycal with a monosubstituted or disubstituted dioxolane and wherein the substituents of said substituted dioxolane are independently selected from the group consisting of H, alkyl, and cycloalkyl.

30. The method of claim 29 wherein
$R_1$ is either H or $CO_2H$,
$R_2$ and $R_3$ are each a $C_7$ straight chain alkyl group, and
$R_4$ and $R_5$ are each H.

31. The method of claim 30 wherein said sugar glycal is either 1,4-anhydro-3-O-benzyl-5,6-cyclopentylidene-2-deoxy-D-lyxo-hex-1-enofuranose or 1,4-anhydro-3-O-benzyl-5,6-cyclopentylidene-2-deoxy-L-! yxo-hex-1-enofuranose.

32. The method of claim 31 wherein said sugar glycal is 1,4-anhydro-3-O-benzyl-5,6-cyclopentylidene-2-deoxy-D-lyxo-hex-1-enofuranose wherein said enofuranose is formed from D-talose.

33. The method of claim 31 wherein said sugar glycal is 1,4-anhydro-3-O-benzyl-5,6-cyclopentylidene-2-deoxy-L-lyxo-hex-1-enofuranose wherein said enofuranose is formed from L-talonic acid-g-lactone.

34. A method for producing a compound having the following structural formula

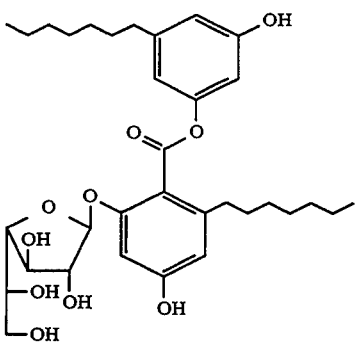

comprising the steps of:
a) providing 1,4-anhydro-3-O-benzyl-5,6-cyclopentylidene-2-deoxy-D-lyxo-hex-1-enofuranose;
b) providing β-trimethylsilylethyl 4-benzyloxy-6-(1-heptyn-1-yl)-2-hydroxy-benzoate;
c) combining the products of steps a) and b) under appropriate conditions to produce [3'-benzyloxy-6'-carboxy-5'-(1-heptyn-1-yl) phenyl]-2,3-di-O-benzyl-5,6-cyclopentylidene-D-galactofuranoside; and
d) combining the product of step c) with 5-heptyl-resorcinol under conditions appropriate for esterification to occur between a resorcinol hydroxyl of said 5-heptyl-resorcinol and the carboxylate moiety of said product of step c), thereby forming compound.

35. The method of claim 34 wherein the 1,4-anhydro-3-O-benzyl-5,6-cyclopentylidene-2-deoxy-D-lyxo-hex-1-enofuranose is synthesized from D-talose and the β-trimethylsilylethyl 4-benzyloxy-6-(1-heptyn-1-yl)2-hydroxy-benzoate and the 5-heptylresorcinol are each synthesized from 2,4,6-trihydroxybenzoic acid.

36. A method for producing a compound having the following structural formula:

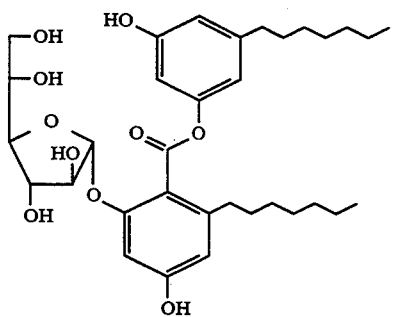

comprising the steps of:
a) providing 1,4-anhydro-3-O-benzyl-5,6-cyclopentylidene-2-deoxy-L-lyxo-hex-1-enofuranose;
b) providing β-trimethylsilylethyl 4-benzyloxy-6-(1-heptyn-1-yl)-2-hydroxy-benzoate;
c) combining the products of steps a) and b) under appropriate conditions to produce [3'-benzyloxy-6'-carboxy-5'-(1-heptyn-1-yl) phenyl]-2,3-di-O-benzyl-5,6-cyclopentylide-ne-L-galactofuranoside; and
d) combining the product of step c) with 5-heptyl-resorcinol under conditions appropriate for esterification to occur between a resorcinol hydroxyl of said 5-heptyl-resorcinol and the carboxylate moiety of said product of step c), thereby forming compound.

37. The method of claim 36 wherein the 1,4-anhydro-3-O-benzyl-5,6-cyclopentylidene-2-deoxy-L-lyxo-hex-1-enofuranose is synthesized from talonic acid-g-lactone and the β-trimethylsilylethyl 4-benzyloxy-6-(1-heptyn-1-yl)-2-hydroxy-benzoate and the 5-heptyl-resorcinol are each synthesized from 2,4,6-trihydroxybenzoic acid.

38. A method for producing a compound having the following structural formula:

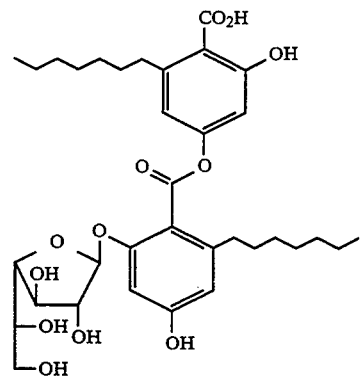

comprising the steps of:
a) providing 1,4-anhydro-3-O-benzyl-5,6-cyclopentylidene-2-deoxy-D-lyxo-hex-1-enofuranose;
b) providing β-trimethylsilylethyl 4-benzyloxy-6-(1-heptyn-1-yl)-2-hydroxy-benzoate;
c) combining the products of steps a) and b) under appropriate conditions to produce [3'-benzyloxy-6'-carboxy-5'-(1-heptyn-1-yl)phenyl]-2,3-di-O-benzyl-5,6-cyclopentylidene-D-galacto-furanoside; and
d) combining the product of step c) with benzyl 2,4-dihydroxy-6-(1-heptyl)-benzoate under conditions appropriate for esterification to occur between the 4-hydroxy of said benzyl 2,4-dihydroxy-6-(1-heptyl)-benzoate and the carboxylate moiety of said product of step c), thereby forming compound.

39. The method of claim 38 wherein the 1,4-anhydro-3-O-benzyl-5,6-cyclopentylidene-2-deoxy-D-lyxo-hex-1-enofuranose is synthesized from D-talose and the β-trimethylsilylethyl 4-benzyloxy-6-(1-heptyn-1-yl)-2-hydroxy-benzoate and the benzyl 2,4-dihydroxy-6-(1-heptyl)-benzoate are each synthesized from 2,4,6-trihydroxybenzoic acid.

40. A method for producing a compound having the following structural formula

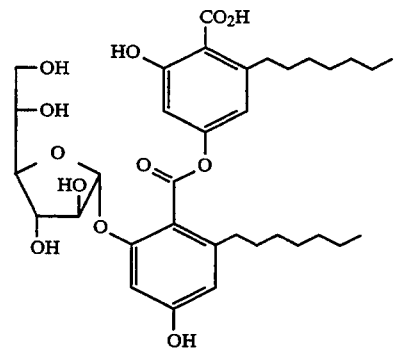

comprising the steps of:
a) providing 1,4-anhydro-3-O-benzyl-5,6-cyclopentylidene-2-deoxy-L-lyxo-hex-1-enofuranose;
b) providing β-trimethylsilylethyl 4-benzyloxy-6-(1-heptyn-1-yl)-2-hydroxy-benzoate;

c) combining the products of steps a) and b) under appropriate conditions to produce [3'-benzyloxy-6'-carboxy-5'-(1-heptyn-1-yl) phenyl]-2,3-di-O-benzyl-5,6-cyclopentylidene-L-galactofuranoside; and d) combining the product of step c) with benzyl 2,4-dihydroxy-6-(1-heptyl)-benzoate under conditions appropriate for esterification to occur between the 4-hydroxy of said benzyl 2,4-dihydroxy-6-(1-heptyl)-benzoate and the carboxylate moiety of said product of step c), thereby forming compound.

41. The method of claim 40 wherein the 1,4-anhydro-3-O-benzyl-5,6-cyclopentylidene-2-deoxy-L-lyxo-hex-1-enofuranose is synthesized from L-talonic acid-g-lactone and the β-trimethylsilylethyl 4-benzyloxy-6-(1-heptyn-1-yl)-2-hydroxy-benzoate and the benzyl 2,4-dihydroxy-6-(1-heptyl)-benzoate are each synthesized from 2,4,6-trihydroxybenzoic acid.

42. A compound having the following structural formula:

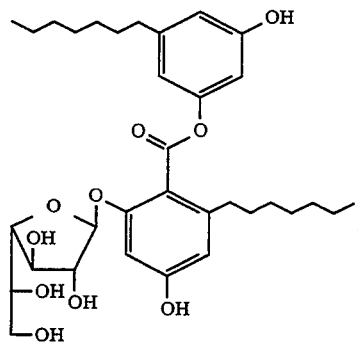

43. A compound having the following structural formula

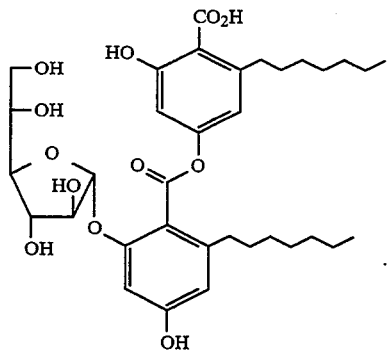

* * * * *

UNITED STATES PATENT AND TRADEMARK OFFICE
CERTIFICATE OF CORRECTION

PATENT NO. : 5,386,019
DATED : January 31, 1995   Page 1 of 2
INVENTOR(S) : Samuel J. Danishefsky, Russell Dushin and William N. Hait It is certified that error appears in the above-indentified patent and that said Letters Patent is hereby corrected as shown below:

Col. 23, Claim 6, line 46: delete "! yxo" and insert --*lyxo*--.
Col. 23, Claim 6, line 47: change "lyxo" to --*lyxo*--.
Col. 23, Claim 7, line 51: delete "! yxo" and insert --*lyxo*--.
Col. 23, Claim 8, line 55: change "lyxo" to --*lyxo*--.
Col. 23, Claim 10, line 63: change "lyxo" to --*lyxo*--.
Col. 23, Claim 10, line 64: change "lyxo" to --*lyxo*--.
Col. 23, Claim 11, line 68: change "lyxo" to --*lyxo*--.
Col. 24, Claim 11, line 1: delete "enfuranose" and insert --enofuranose--.
Col. 24, Claim 13, line 26: change "lyxo" to --*lyxo*--.
Col. 24, Claim 14, line 45: delete "hyptyn" and insert --heptyn--.
Col. 25, Claim 18, line 5: change "lyxo" to --*lyxo*--.
Col. 25, Claim 18, line 5: delete "-1enofuranose" and insert --1-enofuranose--.
Col. 25, Claim 18, line 6: delete "! yxo" and insert --*lyxo*--.
Col. 25, Claim 19, line 12: change "lyxo" to --*lyxo*--.
Col. 25, Claim 20, line 17: change "lyxo" to --*lyxo*--.
Col. 25, Claim 22, line 29: change "lyxo" to --*lyxo*--.
Col. 25, Claim 22, line 30: change "lyxo" to --*lyxo*--.
Col. 25, Claim 23, line 34: change "lyxo" to --*lyxo*--.
Col. 25, Claim 25, line 64: change "lyxo" to --*lyxo*--.
Col. 26, Claim 31, line 52: change "lyxo" to --*lyxo*--.
Col. 26, Claim 31, line 53: delete "! yxo" and insert --*lyxo*--.
Col. 26, Claim 32, line 59: change "lyxo" to --*lyxo*--.
Col. 26, Claim 33, line 64: change "lyxo" to --*lyxo*--.
Col. 27, Claim 34, line 17: change "lyxo" to --*lyxo*--.

UNITED STATES PATENT AND TRADEMARK OFFICE
CERTIFICATE OF CORRECTION

PATENT NO. : 5,386,019

DATED : January 31, 1995

INVENTOR(S) : Samuel J. Danishefsky, Russell Dushin and William N. Hait

It is certified that error appears in the above-indentified patent and that said Letters Patent is hereby corrected as shown below:

Col. 27, Claim 34, line 29:   before "compound", insert --said--.
Col. 27, Claim 35, line 31:   change "lyxo" to --*lyxo*--.
Col. 27, Claim 36, line 53:   change "lyxo" to --*lyxo*--.
Col. 27, Claim 36, line 66:   before "compound", insert --said--.
Col. 27, Claim 37, line 68:   change "lyxo" to --*lyxo*--.
Col. 28, Claim 38, line 25:   change "lyxo" to --*lyxo*--.
Col. 28, Claim 38, line 39:   before "compound", insert --said--.
Col. 28, Claim 39, line 41:   change "lyxo" to --*lyxo*--.
Col. 28, Claim 40, line 66:   change "lyxo" to --*lyxo*--.
Col. 29, Claim 40, line 17:   before "compound", insert --said .
Col. 29, Claim 41, line 21:   change "lyxo" to --*lyxo*--.

Signed and Sealed this

Second Day of May, 1995

BRUCE LEHMAN

Attest:

*Attesting Officer*         *Commissioner of Patents and Trademarks*